United States Patent
Bae et al.

(10) Patent No.: US 9,000,176 B2
(45) Date of Patent: Apr. 7, 2015

(54) PYRAZOLE DERIVATIVES, PREPARATION METHOD THEREOF, AND COMPOSITION FOR PREVENTION AND TREATMENT OF OSTEOPOROSIS CONTAINING SAME

(71) Applicant: Ewha University—Industry Collaboration Foundation, Seoul (KR)

(72) Inventors: Yun Soo Bae, Seongnam-si (KR); Jee Hyun Lee, Seoul (KR); Mi Sun Seo, Seoul (KR); Soo Young Lee, Seoul (KR); Sun Choi, Seoul (KR); Kee In Lee, Daejeon (KR); Hye Rin Bin, Busan (KR); Do Min Lee, Daejeon (KR)

(73) Assignee: Ewha University—Industry Collaboration Foundation, Seoul (KR)

( * ) Notice: Subject to any disclaimer, the term of this patent is extended or adjusted under 35 U.S.C. 154(b) by 0 days.

(21) Appl. No.: 14/073,601

(22) Filed: Nov. 6, 2013

(65) Prior Publication Data

US 2014/0066404 A1 Mar. 6, 2014

Related U.S. Application Data

(63) Continuation of application No. 13/393,794, filed as application No. PCT/KR2010/005974 on Sep. 2, 2010, now Pat. No. 8,604,210.

(30) Foreign Application Priority Data

Sep. 2, 2009 (KR) ........................ 10-2009-0082517

(51) Int. Cl.
*A61K 31/44* (2006.01)
*C07D 401/00* (2006.01)
*C07F 7/08* (2006.01)
*C07D 401/04* (2006.01)
*C07D 403/04* (2006.01)
*C07D 405/14* (2006.01)
*C07F 5/02* (2006.01)

(52) U.S. Cl.
CPC ............ *C07F 7/0812* (2013.01); *C07D 401/04* (2013.01); *C07D 403/04* (2013.01); *C07D 405/14* (2013.01); *C07F 5/025* (2013.01)

(58) Field of Classification Search
CPC ...................................................... C07D 401/04
See application file for complete search history.

(56) References Cited

U.S. PATENT DOCUMENTS 5,175,176 A 12/1992 Sasse et al.
5,292,744 A * 3/1994 Sasse et al. ................... 514/275

FOREIGN PATENT DOCUMENTS

EP 2 050 745 A1 4/2009

OTHER PUBLICATIONS

Boyle et al., "Osteoclast differentiation and activation," *Nature* 423(6937):337-342, May 15, 2003.
Darden et al., "Osteoclastic Superoxide Production and Bone Resorption: Stimulation and Inhibition by Modulators of NADPH Oxidase," *Journal of Bone and Mineral Research* 11(5):671-675, 1996.
Fraser et al., "Hydrogen Peroxide, But Not Superoxide, Stimulates Bone Resorption in Mouse Calvariae," *Bone* 19(3):223-226, Sep. 1996.
Oikawa et al., "Meldrum's Acid in Organic Synthesis. 2. A General and Versatile Synthesis of β-Keto Esters," *Journal of Organic Chemistry* 43(10):2087-2088, May 1, 1978.
Yang et al., "A New Superoxide-generating Oxidase in Murine Osteoclasts," *Journal of Biological Chemistry* 276(8):5452-5458, 2001.
Yang et al., "Nicotinamide Adenine Dinucleotide Phosphate Oxidase in the Formation of Superoxide in Osteoclasts," *Calcified Tissue International* 63(4):346-350, Oct. 1998.

* cited by examiner

*Primary Examiner* — Heidi Reese
(74) *Attorney, Agent, or Firm* — Seed IP Law Group PLLC

(57) ABSTRACT

The present invention provides pyrazole derivative compounds and pharmaceutically acceptable salts thereof. The compounds of the present invention have an excellent effect of preventing and treating osteoporosis.

19 Claims, 4 Drawing Sheets

PYRAZOLE DERIVATIVES, PREPARATION METHOD THEREOF, AND COMPOSITION FOR PREVENTION AND TREATMENT OF OSTEOPOROSIS CONTAINING SAME

TECHNICAL FIELD

The present invention relates to a novel pyrazole derivative having excellent inhibitory activity against reactive oxygen species, a method for preparing the same, and a composition for the prevention and treatment of osteoporosis containing the same.

BACKGROUND ART

The process of bone modeling and remodeling plays an important role in development, growth and metabolism of bone. Bone modeling initiates from birth and then continues until adolescence/manhood at which time the skeleton matures to an end of growth of an individual, thus achieving the peak bone mass from between his/her twenties to early-thirties. Since then, a bone remodeling process involving removal and replacement of bone is repeated for about 3 years, during which bone formation and bone resorption are coupled to maintain the balance therebetween. After this period of time, bone formation cannot sufficiently keep up with bone loss occurring due to bone resorption, which eventually results in an about 0.3 to 0.5% annual decrease in bone mass. In particular, women will undergo a significant bone loss of 2 to 3% yearly at the early stage of menopause.

Bone consists mainly of four cell types, namely, osteoblasts, osteoclasts, lining cells and osteocytes. Here, osteoblasts, which are derived from bone marrow stromal cells, are differentiated cells of synthesizing a bone matrix and play a leading part in bone formation, whereas osteoclasts, which are derived from hematopoietic stem cells, play a leading part in bone resorption.

Osteoporosis is a condition in which a calcified bone tissue density is decreased and thus the compact substance of bone is lost gradually, leading to broadening of the marrow cavity. As osteoporosis progresses, bone becomes fragile and consequently bone fractures may readily occur even with a small impact. Bone mass is affected by a variety of factors including genetics, nutrition, hormonal changes, physical exercise and lifestyle habits. Aging, insufficient exercise, being underweight, smoking, low-calcium dietary intake, menopause and ovariectomy are known as pathogenic causes of osteoporosis. Although there is a difference among individuals, it is known that black people exhibit a lower bone resorption level than white people, thus meaning that black people have a higher bone mass. The peak bone mass is generally observed between age 14 and 18, and then the bone mass decreases with aging at a rate of about 1% per year. In particular, bone is continuously decreased from the age of 30 in women and is rapidly reduced due to hormonal changes after menopause. In other words, when reaching the perimenopausal period, a level of estrogen is rapidly decreased. At this time, large numbers of B-lymphocytes are formed as if it happened by interleukin-7 (IL-7), and pre-B cells are accumulated in bone marrow, which consequently leads to an increase in the level of IL-6, thus resulting in an increased activity of osteoclasts and finally a decreased level of bone mass.

As described above, osteoporosis, although showing a difference in terms of disease severity to a certain extent, is inevitable in the aged, especially in post-menopausal women, so osteoporosis and its therapeutic agents have increasingly become the center of interest as the aging population grows in advanced countries. The treatment of bone diseases forms an approximately 130 billion dollar-market throughout the world, which is assumed to grow further. Thus, numbers of worldwide research institutions and pharmaceutical companies have invested heavily in development of therapeutic agents for the treatment of bone diseases. Also recently in Korea, the morbidity of osteoporosis has begun to rapidly soar as the average span of human life comes close to 80 years. According to research recently conducted for local residents, when the research results are normalized in terms of total population, it has been reported that 4.5% of males have osteoporosis and 19.8% of females suffer from the same disease. These results suggest that osteoporosis is a more common disease than diabetes or cardiovascular diseases and when considering the suffering of patients due to fractures or when estimating costs incurred for the treatment of a disease, osteoporosis is a very important public health problem.

Many kinds of substances have been developed hitherto as anti-osteoporosis agents. Among those therapeutic substances, estrogen, which is most commonly used as an anti-osteoporosis agent but whose practical efficacy has not yet been demonstrated, disadvantageously requires life-time administration, and long-term administration thereof may result in adverse side effects such as increased risk of breast cancer or uterine cancer. Alendronate also has problems associated with indefinite understanding of medicinal efficacy, sluggish gastrointestinal absorption, and pathogenesis of inflammation on gastrointestinal and esophageal mucosa. Calcium preparations are known to exhibit superior therapeutic effects with lower adverse side effects but are limited to prevention rather than treatment. Incidentally, vitamin D preparations, such as calcitonin, are known, but efficacy and adverse side effects thereof have not yet been sufficiently investigated. To this end, there is a need for the development of a novel therapeutic agent for the treatment of metabolic bone diseases which exhibits excellent therapeutic effects and a low rate of adverse side effects.

Meanwhile, studies have recently been reported showing that reactive oxygen species (ROS) generated due to oxidative stress are involved in metabolism of bone (Darden, A. G., et al., J. Bone Miner, Res., 11:671-675, 1996; Yang, S., et al., J. Biol. Chem., 276:5452-5458, 2001; Fraser, J. H., et al., Bone 19:223-226, 1996; and Yang, S., et al., Calcif. Tissue Int., 63:346-350, 1998). Further, it is known that bone remodeling is carried out through the relative action between bone-forming osteoblasts and bone-resorbing osteoclasts. Multinuclear osteoclasts are differentiated from a monocyte/macrophage lineage of hematopoietic progenitor cells through a multi-stage process of cell adhesion, proliferation, motility, cell-cell contact and terminal fusion for the formation of multinucleated giant cells. This process is initiated by binding of a receptor activator of nuclear factor-kB ligand (hereinafter, referred to as "RANKL") to a receptor activator of nuclear factor-kB (hereinafter, referred to as "RANK") and is then transmitted through the activation of several signaling cascades. The activated signaling pathway includes NF-KB, extracellular signal-regulated kinase (hereinafter, referred to as "ERK"), c-Jun N-terminal kinase (hereinafter, referred to as "JNK") and p38 mitogen-activated protein (MAP) kinase through a tumor necrosis factor (TNF) receptor-associated factor 6 (hereinafter, referred to as "TRAF6"). Such a signaling event has a direct effect on the modulation of differentiation and action of osteoclasts (Boyle, N. J., et al., Nature, 423:337-342, 2003). Once osteoclasts are differentiated, the resorption of bone is accelerated by ROS generated due to nicotinamide adenine dinucleotide phosphate (NADPH) oxidase. An NADPH oxidase inhibitor leads to a reduction of ROS and bone resorption (Yang, S., et al., Calcif. Tissue Int., 63:346-350, 1998). These results are consistent with the theory suggesting that the generation of ROS in osteoclasts is dependent on the activity of NADPH oxidase and is directly connected with the function of osteoclasts.

Therefore, the inventors of the present invention have conducted extensive and intensive studies based on the idea that an anti-osteoporosis agent may be developed by taking advantage of a molecular mechanism which inhibits the generation of ROS and found that pyrazole derivatives of the present invention exhibit excellent inhibitory activity on the generation of ROS and these compounds may be used for the prevention or treatment of osteoporosis.

DISCLOSURE OF THE INVENTION

Technical Problem

Therefore, an object of the present invention is to provide a novel pyrazole derivative having excellent inhibitory activity on the generation of reactive oxygen species, a method for preparing the same, and a composition for the treatment of osteoporosis containing the same.

It is another object of the present invention to provide a method for preventing or treating osteoporosis, including administering a novel pyrazole derivative of the present invention to a subject in need thereof, and use of a novel pyrazole derivative of the present invention for the preparation of a pharmaceutical formulation for preventing or treating osteoporosis.

Technical Solution

The present invention provides a compound of formula I or a pharmaceutically acceptable salt thereof:

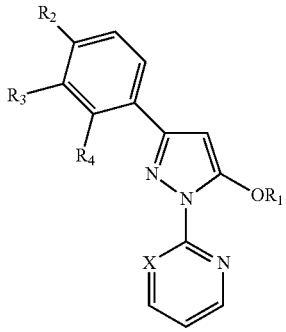

[Formula I]

wherein X represents —CH— or nitrogen;

$R_1$ represents a hydrogen atom, an acetyl group, a tri($C_1$-$C_4$) alkylsilanyl group, a diphenylboranyl group or a (t-butoxy)carbonyl group; and $R_2$, $R_3$ and $R_4$ each independently represent a hydrogen atom, a halogen atom (F, Cl, Br, I), a halo($C_1$-$C_3$) alkyl group, a ($C_2$-$C_6$) alkoxy group, a benzo[d][1,3]dioxole group, an unsubstituted or substituted biphenyl group or an unsubstituted or substituted ($C_6$-$C_{10}$) aryl group, wherein the substituent is a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group or a halogen-substituted phenyl group, provided that all of $R_2$, $R_3$ and $R_4$ are not a hydrogen atom at the same time.

In formula I of the present invention, preferred is a compound of formula I wherein X represents —CH—; $R_1$ represents a hydrogen atom, an acetyl group, a tri($C_1$-$C_4$) alkylsilanyl group, a diphenylboranyl group or a (t-butoxy)carbonyl group; and $R_2$, $R_3$ and $R_4$ each independently represent a hydrogen atom, a halogen atom, a benzo[d][1,3]dioxole group, an unsubstituted or substituted biphenyl group or an unsubstituted or substituted phenyl group, wherein the substituent is a halogen atom or a phenoxy group, provided that all of $R_2$, $R_3$ and $R_4$ are not a hydrogen atom at the same time; or a pharmaceutically acceptable salt thereof.

In formula I of the present invention, more preferred is a compound of formula I wherein X represents —CH—, $R_1$ represents a hydrogen atom, an acetyl group, a tri($C_1$-$C_4$) alkylsilanyl group or a diphenylboranyl group; and $R_2$, $R_3$ and $R_4$ each independently represent a hydrogen atom, a halogen atom, a benzo[d][1,3]dioxole group, a biphenyl group or an unsubstituted or substituted phenyl group wherein the substituent is a halogen atom or a phenoxy group, provided that all of $R_2$, $R_3$ and $R_4$ are not a hydrogen atom at the same time; or a pharmaceutically acceptable salt thereof.

The compound of the present invention is preferably a compound or a pharmaceutically acceptable salt thereof selected from:

1-(pyridin-2-yl)-3-(3-(trifluoromethyl)phenyl)-1H-pyrazol-5-ol,
1-(pyridin-2-yl)-3-(4-(trifluoromethyl)phenyl)-1H-pyrazol-5-ol,
3-(3-nitrophenyl)-1-(pyridin-2-yl)-1H-pyrazol-5-ol,
1-(pyridin-2-yl)-3-(3,4,5-trimethoxyphenyl)-1H-pyrazol-5-ol,
3-(2-fluorophenyl)-1-(pyridin-2-yl)-1H-pyrazol-5-ol,
3-(3-fluorophenyl)-1-(pyridin-2-yl)-1H-pyrazol-5-ol,
3-(4-fluorophenyl)-1-(pyridin-2-yl)-1H-pyrazol-5-ol,
3-(2-chlorophenyl)-1-(pyridin-2-yl)-1H-pyrazol-5-ol,
3-(3-chlorophenyl)-1-(pyridin-2-yl)-1H-pyrazol-5-ol,
3-(4-chlorophenyl)-1-(pyridin-2-yl)-1H-pyrazol-5-ol,
3-(3-bromophenyl)-1-(pyridin-2-yl)-1H-pyrazol-5-ol,
3-(4-bromophenyl)-1-(pyridin-2-yl)-1H-pyrazol-5-ol,
3-(2-iodophenyl)-1-(pyridin-2-yl)-1H-pyrazol-5-ol,
3-(3-iodophenyl)-1-(pyridin-2-yl)-1H-pyrazol-5-ol,
3-(4-iodophenyl)-1-(pyridin-2-yl)-1H-pyrazol-5-ol,
3-(4-iodophenyl)-1-(pyrimidin-2-yl)-1H-pyrazol-5-ol,
2-(3-(4-iodophenyl)-5-(triisopropylsilyloxy)-1H-pyrazol-1-yl)pyridine,
3-(4-bromophenyl)-1-(pyridin-2-yl)-1H-pyrazol-5-yl tert-butyl carbonate,
tert-butyl 3-(2-iodophenyl)-1-(pyridin-2-yl)-1H-pyrazol-5-yl carbonate,
tert-butyl 3-(3-iodophenyl)-1-(pyridin-2-yl)-1H-pyrazol-5-yl carbonate,
tert-butyl 3-(4-iodophenyl)-1-(pyridin-2-yl)-1H-pyrazol-5-yl carbonate,
tert-butyl 3-(4-iodophenyl)-1-(pyrimidin-2-yl)-1H-pyrazol-5-yl carbonate,
3-(4-bromophenyl)-1-(pyridin-2-yl)-1H-pyrazol-5-yl acetate,
3-(biphenyl-4-yl)-1-(pyridin-2-yl)-1H-pyrazol-5-yl tert-butyl carbonate,
3-(4-(benzo[d][1,3]dioxol-5-yl)phenyl)-1-(pyridin-2-yl)-1H-pyrazol-5-yl tert-butyl carbonate,
3-(3'-phenylbiphenyl-4-yl)-1-(pyridin-2-yl)-1H-pyrazol-5-yl tert-butyl carbonate,
tert-butyl 3-(4-(naphthalene)phenyl)-1-(pyridin-2-yl)-1H-pyrazol-5-yl carbonate,
tert-butyl 3-(3'-(dimethylamino)biphenyl)-1-(pyridin-2-yl)-1H-pyrazol-5-yl carbonate, 3-(2-(benzo[d][1,3]dioxol-5-yl)phenyl)-1-(pyridin-2-yl)-1H-pyrazol-5-yl tert-butyl carbonate,
3-(3'-phenylbiphenyl-2-yl)-1-(pyridin-2-yl)-1H-pyrazol-5-yl tert-butyl carbonate,
3-(biphenyl-3-yl)-1-(pyridin-2-yl)-1H-pyrazol-5-yl tert-butyl carbonate,
3-(4'-(benzyloxy)biphenyl-3-yl)-1-(pyridin-2-yl)-1H-pyrazol-5-yl tert-butyl carbonate,
3-(4'-bromobiphenyl-3-yl)-1-(pyridin-2-yl)-1H-pyrazol-5-yl tert-butyl carbonate,
tert-butyl 3-(3'-formylbiphenyl-3-yl)-1-(pyridin-2-yl)-1H-pyrazol-5-yl carbonate,
tert-butyl 3-(2'-phenoxybiphenyl-3-yl)-1-(pyridin-2-yl)-1H-pyrazol-5-yl carbonate,
3-(3-(benzo[d][1,3]dioxol-5-yl)phenyl)-1-(pyridin-2-yl)-1H-pyrazol-5-yl tert-butyl carbonate,
3-(3'-phenylbiphenyl-3-yl)-1-(pyridin-2-yl)-1H-pyrazol-5-yl tert-butyl carbonate,
tert-butyl 3-(3-(naphthalen-1-yl)phenyl)-1-(pyridin-2-yl)-1H-pyrazol-5-yl carbonate,
tert-butyl 3-(3'-(dimethylamino)biphenyl-3-yl)-1-(pyridin-2-yl)-1H-pyrazol-5-yl carbonate,
tert-butyl 3-(4'-methoxybiphenyl-4-yl)-1-(pyridin-2-yl)-1H-pyrazol-5-yl carbonate,
3-(4'-(benzyloxy)biphenyl-4-yl)-1-(pyridin-2-yl)-1H-pyrazol-5-yl tert-butyl carbonate,
3-(4'-bromobiphenyl-4-yl)-1-(pyridin-2-yl)-1H-pyrazol-5-yl tert-butyl carbonate,
3-(3'-formylbiphenyl-4-yl)-1-(pyridin-2-yl)-1H-pyrazol-5-yl tert-butyl carbonate,
tert-butyl 3-(2'-phenoxybiphenyl-4-yl)-1-(pyridin-2-yl)-1H-pyrazol-5-yl carbonate,
3-(biphenyl-4-yl)-1-(pyrimidin-2-yl)-1H-pyrazol-5-yl tert-butyl carbonate,
3-(4-(benzo[d][1,3]dioxol-5-yl)phenyl)-1-(pyrimidin-2-yl)-1H-pyrazol-5-yl tert-butyl carbonate,
3-(3'-phenylbiphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(3'-phenylbiphenyl-4-yl)-1-(pyridin-2-yl)-1H-pyrazol-5-ol,
3-(4-(naphthalen-1-yl)phenyl)-1-(pyridin-2-yl)-1H-pyrazol-5-ol,
3-(3'-(dimethylamino)biphenyl-4-yl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(3'-phenylbiphenyl-2-yl)-1-(pyridin-2-yl)-1H-pyrazol-5-ol,
3-(biphenyl-3-yl)-1-(pyridin-2-yl)-1H-pyrazol-5-ol,
3-(4'-(benzyloxy)biphenyl-3-yl)-1-(pyridin-2-yl)-1H-pyrazol-5-ol,
3-(4'-bromobiphenyl-3-yl)-1-(pyridin-2-yl)-1H-pyrazol-5-ol,
3-(3'-formylbiphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3-(benzo[d][1,3]dioxol-5-yl)phenyl)-1-(pyridin-2-yl)-1H-pyrazol-5-ol,
3-(3'-phenylbiphenyl-3-yl)-1-(pyridin-2-yl)-1H-pyrazol-5-ol,
3-(3-(naphthalen-1-yl)phenyl)-1-(pyridin-2-yl)-1H-pyrazol-5-ol,
3-(3'-(dimethylamino)biphenyl-3-yl)-1-(pyridin-2-yl)-1H-pyrazol-5-ol,
3-(4'-methoxybiphenyl-4-yl)-1-(pyridin-2-yl)-1H-pyrazol-5-ol,
3-(4'-(benzyloxy)biphenyl-4-yl)-1-(pyridin-2-yl)-1H-pyrazol-5-ol,
3-(4'-bromobiphenyl-4-yl)-1-(pyridin-2-yl)-1H-pyrazol-5-ol,
3-(3'-formylbiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol,
3-(biphenyl-4-yl)-1-(pyrimidin-2-yl)-1H-pyrazol-5-ol,
3-(4-(benzo[d][1,3]dioxol-5-yl)phenyl)-1-(pyrimidin-2-yl)-1H-pyrazol-5-ol,
3-(3'-phenylbiphenyl-4-yl)-1-(pyrimidin-2-yl)-1H-pyrazol-5-ol,
3-phenyl-4-propyl-1-(pyridin-2-yl)-1H-pyrazol-5-ol, and
4-benzyl-3-phenyl-1-(pyridin-2-yl)-1H-pyrazol-5-ol.

The compound of the present invention is more preferably a compound or a pharmaceutically acceptable salt thereof selected from:
3-(4-bromophenyl)-1-(pyridin-2-yl)-1H-pyrazol-5-ol,
3-(2-iodophenyl)-1-(pyridin-2-yl)-1H-pyrazol-5-ol,
3-(3-iodophenyl)-1-(pyridin-2-yl)-1H-pyrazol-5-ol,
3-(4-iodophenyl)-1-(pyridin-2-yl)-1H-pyrazol-5-ol,
3-(4-iodophenyl)-1-(pyrimidin-2-yl)-1H-pyrazol-5-ol,
2-(3-(4-iodophenyl)-5-(triisopropylsilyloxy)-1H-pyrazol-1-yl)pyridine,
3-(4-bromophenyl)-1-(pyridin-2-yl)-1H-pyrazol-5-yl acetate,
3-(biphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(biphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3'-phenylbiphenyl-3-yl)-1-(pyridin-2-yl)-1H-pyrazol-5-ol,
3-(4'-bromobiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol,
3-(biphenyl-4-yl)-1-(pyrimidin-2-yl)-1H-pyrazol-5-ol,
3-phenyl-4-propyl-1-(pyridin-2-yl)-1H-pyrazol-5-ol, and
4-benzyl-3-phenyl-1-(pyridin-2-yl)-1H-pyrazol-5-ol.

As used herein, the term "pharmaceutically acceptable salt" refers to a salt commonly used in the pharmaceutical industry, and examples thereof include a salt with an inorganic ion such as calcium, potassium, sodium, or magnesium; a salt with an inorganic acid such as hydrochloric acid, nitric acid, phosphoric acid, bromic acid, iodic acid, perchloric acid, tartaric acid, or sulfuric acid; a salt with an organic acid such as acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, or hydroiodic acid; a salt with sulfonic acid such as methanesulfonic acid, ethanesulfonic acid, benzenesulfonic acid, p-toluenesulfonic acid, or naphthalene sulfonic acid; a salt with amino acid such as glycine, arginine, or lysine; and a salt with amine such as trimethylamine, triethylamine, ammonia, pyridine, or picoline. However, the present invention is not limited thereto.

The compound of formula I, the above-exemplified compound or a pharmaceutically acceptable salt thereof in accordance with the present invention is capable of preventing or treating osteoporosis by inhibiting the generation of reactive oxygen species. For example, the compound of formula I, the above-exemplified compound or a pharmaceutically acceptable salt thereof in accordance with the present invention is capable of inhibiting the generation of reactive oxygen species by inhibiting NADPH oxidase. The production of osteoclasts may be inhibited through the inhibition of NADPH oxidase which is an important substance for differentiation of macrophages into osteoclasts.

The compound of formula I, the above-exemplified compound or a pharmaceutically acceptable salt thereof in accordance with the present invention is capable of treating or preventing osteoporosis through inhibition of osteoclast formation.

Further, the present invention provides a method for preparing a compound of formula I-1, including heating a compound of formula II and a compound of formula III in a polar organic solvent.

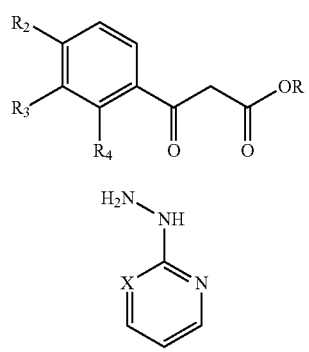

[Formula II]

[Formula III]

wherein X represents —CH— or nitrogen;

R represents a $(C_1-C_4)$ alkyl group; and $R_2$, $R_3$ and $R_4$ each independently represent a hydrogen atom, a halogen atom, a halo$(C_1-C_3)$ alkyl group or a $(C_2-C_6)$ alkoxy group, provided that all of $R_2$, $R_3$ and $R_4$ are not a hydrogen atom at the same time.

In the method for preparing a compound of formula I-1 in accordance with the present invention, β-keto ester, which is the compound of formula II as used as a starting material, is commercially available or may be prepared according to the method described in J. Org. Chem., Vol. 43, No. 10, 1978, 2087-2088, specifically by reacting a commercially available acyl chloride derivative with Meldrum's acid and heating the resulting product under reflux, in the presence of a methanol or ethanol solvent.

In the method for preparing a compound of formula I-1 in accordance with the present invention, the compound of formula III which is a reactant may be commercially available and may be used in an amount of about 1 to 3 molar equivalents and preferably 1 to 1.3 molar equivalents, based on 1 molar equivalent of the compound of formula II which is a starting material.

In the method for preparing a compound of formula I-1 in accordance with the present invention, the polar organic solvent is preferably selected from $C_1$-$C_4$ alcohol such as methanol, ethanol, n-propanol, i-isopropanol, n-butanol or t-butanol, acetic acid and a mixture thereof. Ethanol or acetic acid is more preferred.

In the method for preparing a compound of formula I-1 in accordance with the present invention, heating is carried out at a temperature capable of refluxing a solvent. For example, heating is preferably carried out at a temperature of about 100 to about 130° C.

In the method for preparing a compound of formula I-1 in accordance with the present invention, the reaction is preferably carried out for 2 to 72 hours.

Further, the present invention provides a method for preparing a compound of formula I-2, including reacting a compound of formula I-1 with one compound selected from acetyl chloride, tris$(C_1-C_4)$ alkylsilyl chloride and di-tert-butyl dicarbonate (BOC$_2$O), in the presence of a base.

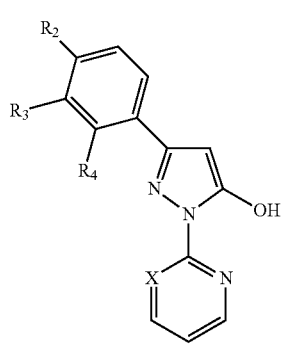

Formula [I-1]

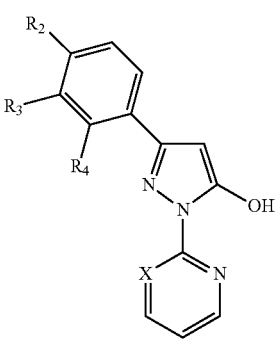

[Formula I-1]

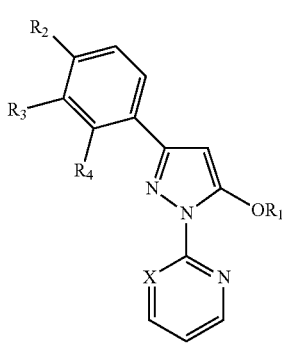

[Formula I-2]

wherein X represents —CH— or nitrogen;

$R_1$ represents an acetyl group, a tri($C_1$-$C_4$) alkylsilyl group or a (t-butoxy)carbonyl group; and $R_2$, $R_3$ and $R_4$ each independently represent a hydrogen atom, a halogen atom, a halo($C_1$-$C_3$) alkyl group or a ($C_2$-$C_6$) alkoxy group, provided that all of $R_2$, $R_3$ and $R_4$ are not a hydrogen atom at the same time.

In the method for preparing a compound of formula I-2 in accordance with the present invention, acetyl chloride, tris ($C_1$-$C_4$) alkylsilyl chloride or di-tert-butyl dicarbonate ($BOC_2O$) which is a reactant is preferably used in an amount of 1.2 to 5 equivalents based on 1 equivalent of the compound of formula I-1 which is a starting material.

In the method for preparing a compound of formula I-2 in accordance with the present invention, the base is preferably selected from 4-dimethylaminopyridine (DMAP), pyridine, triethylamine and imidazole, and the catalyst is more preferably 4-dimethylaminopyridine. Here, the base is preferably used in an amount of 2 to 3 equivalents. The catalyst is preferably used in an amount of 0.01 to 0.5 molar equivalents and more preferably 0.05 molar equivalents, based on 1 molar equivalent of the compound of formula I-1 which is a starting material.

In the method for preparing a compound of formula I-2 in accordance with the present invention, the reaction solvent may be, for example, an organic solvent such as methylene chloride, ethyl ether, ethyl acetate, tetrahydrofuran (THF) or N,N'-dimethylformamide (DMF). Methylene chloride is preferred.

In the method for preparing a compound of formula I-2 in accordance with the present invention, the reaction temperature is preferably in the range of about 0 to about 40° C., more preferably 15 to 30° C., and the reaction time is preferably in the range of 10 to 12 hours. Depending on the reaction rate, the reaction temperature may be further elevated and the reaction time may be further increased.

Further, the present invention provides a method for preparing a compound of formula I-3, including reacting a compound of formula I-2 with a compound of formula IV in the presence of a palladium metal catalyst and a base.

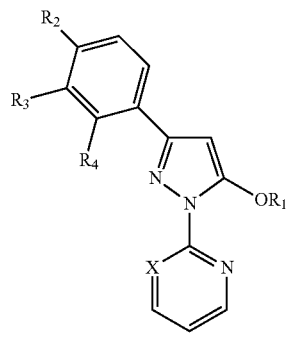

[Formula I-2]

wherein X represents —CH— or nitrogen;

$R_1$ represents hydrogen, an acetyl group, a tri($C_1$-$C_4$) alkylsilanyl group or a (t-butoxy)carbonyl group; and $R_2$, $R_3$ and $R_4$ each independently represent a hydrogen atom or a halogen atom, provided that all of $R_2$, $R_3$ and $R_4$ are not a hydrogen atom at the same time;

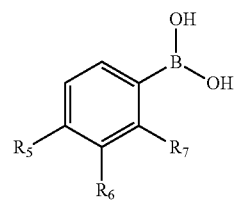

[Formula IV]

wherein $R_5$, $R_6$ and $R_7$ each independently represent a hydrogen atom, a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group, a phenyl group or a halogen-substituted phenyl group, or alternatively $R_5$ and $R_6$ or $R_6$ and $R_7$ represent —$OCH_2O$— or —CH=CH—CH=CH—, provided that all of $R_5$, $R_6$ and $R_7$ are not a hydrogen atom at the same time;

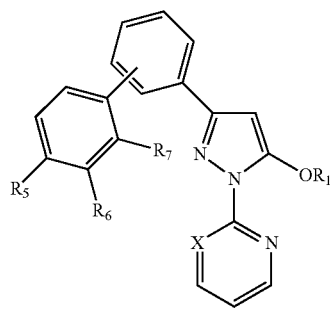

[Formula I-3]

wherein X represents —CH— or nitrogen;

$R_1$ represents hydrogen, an acetyl group, a tri($C_1$-$C_4$) alkylsilanyl group, a diphenylboranyl group or a (t-butoxy)carbonyl group; and $R_5$, $R_6$ and $R_7$ each independently represent a hydrogen atom, a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group, a phenyl group or a halogen-substituted phenyl group, or alternatively $R_5$ and $R_6$ or $R_6$ and R$_7$ represent —OCH$_2$O— or —CH=CH—CH=CH—, provided that all of R$_5$, R$_6$ and R$_7$ are not a hydrogen atom at the same time.

In the method for preparing a compound of formula I-3 in accordance with the present invention, the compound of formula IV which is a reactant may be commercially available. The compound of formula IV which is a reactant is preferably used in an amount of about 1 to 5 equivalents and more preferably 2 to 3 equivalents, based on 1 equivalent of the compound of formula I-2.

In the method for preparing a compound of formula I-3 in accordance with the present invention, the palladium metal catalyst is 1,1'-bis(diphenylphosphino)ferrocene (dppf) and PdCl$_2$(dppf), or examples of the Pd catalyst that may be used include Pd(PPh$_3$)$_4$, Pd(OAc)$_2$, and Pd(dba)CHCl$_3$. PdCl$_2$(dppf) and, 1,1'-bis(diphenylphosphino)ferrocene (dppf) and PdCl$_2$(dppf) are preferred. Here, the palladium metal catalyst is preferably used in an amount of 0.01 to 0.5 equivalents and more preferably 0.03 to 0.1 equivalents, based on 1 equivalent of the compound of formula I-2. Incidentally, PdCl$_2$(dppf) and dppf are preferably used in an equivalent ratio of 2:1.

In the method for preparing a compound of formula I-3 in accordance with the present invention, the base is preferably selected from K$_3$PO$_4$, K$_2$CO$_3$, Ba(OH)$_2$ and Cs$_2$CO$_3$, and is preferably used in an amount of 1 to 3 molar equivalents, based on 1 molar equivalent of the compound of formula I-2.

In the method for preparing a compound of formula I-3 in accordance with the present invention, the reaction temperature is preferably in the range of 90 to 110° C. and the reaction solvent is preferably selected from 1,4-dioxane, THF, DMF and toluene.

Further, the present invention provides a method for converting a compound of formula I-3 into a compound of formula I-4 in the presence of an organic acid.

[Formula I-3]

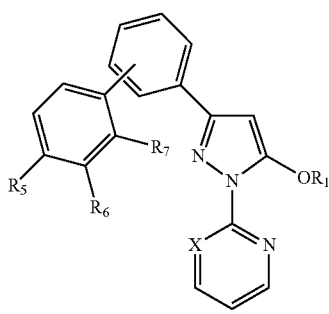

[Formula I-4]

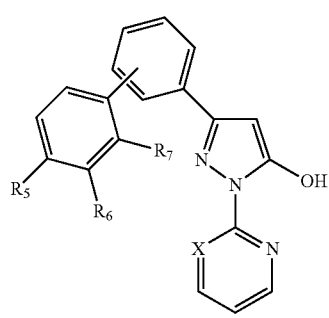

wherein X represents —CH— or nitrogen;
R$_1$ represents an acetyl group, a tri(C$_1$-C$_4$) alkylsilanyl group or a (t-butoxy)carbonyl group;
R$_5$, R$_6$ and R$_7$ each independently represent a hydrogen atom, a halogen atom, a (C$_1$-C$_4$) alkylamine group, a halo(C$_1$-C$_3$) alkyl group, a (C$_1$-C$_6$) alkoxy group, a phenoxy group, a benzyloxy group, a formyl group, a phenyl group or a halogen-substituted phenyl group, or alternatively R$_5$ and R$_6$ or R$_6$ and R$_7$ represent —OCH$_2$O— or —CH=CH—CH=CH—, provided that all of R$_5$, R$_6$ and R$_7$ are not a hydrogen atom at the same time.

In the method for preparing a compound of formula I-4 in accordance with the present invention, the organic acid is preferably selected from trifluoroacetic acid, trichloroacetic acid, HF and HCl. Trifluoroacetic acid is more preferred. Here, the organic acid is preferably used in an amount of about 2 to 10 equivalents and more preferably 4 to 6 equivalents, based on 1 equivalent of the compound of formula I-3.

In the method for preparing a compound of formula I-4 in accordance with the present invention, the reaction temperature is preferably in the range of about 0 to 40° C. and more preferably 15 to 30° C. The reaction solvent is preferably selected from methylene chloride, THF, chloroform and dichloroethane.

Further, the present invention provides a pharmaceutical composition for the prevention or treatment of osteoporosis, containing a compound of formula I or a pharmaceutically acceptable salt thereof:

[Formula I]

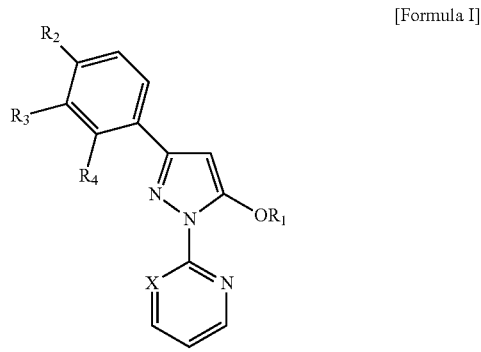

wherein X represents —CH— or nitrogen;
R$_1$ represents a hydrogen atom, an acetyl group, a tri(C$_1$-C$_4$) alkylsilanyl group, a diphenylboranyl group or a (t-butoxy)carbonyl group; and
R$_2$, R$_3$ and R$_4$ each independently represent a hydrogen atom, a halogen atom, a halo(C$_1$-C$_3$) alkyl group, a (C$_1$-C$_6$) alkoxy group, a benzo[d][1,3]dioxole group, an unsubstituted or substituted biphenyl group or an unsubstituted or substituted (C$_6$-C$_{10}$) aryl group, wherein the substituent is a halogen atom, a (C$_1$-C$_4$) alkylamine group, a halo(C$_1$-C$_3$) alkyl group, a (C$_1$-C$_6$) alkoxy group, a phenoxy group, a benzyloxy group, a formyl group or a halogen-substituted phenyl group, provided that all of R$_2$, R$_3$ and R$_4$ are not a hydrogen atom at the same time.

Further, the present invention provides a composition for the prevention or treatment of osteoporosis, containing a compound or a pharmaceutically acceptable salt thereof selected from:
1-(pyridin-2-yl)-3-(3-(trifluoromethyl)phenyl)-1H-pyrazol-5-ol,
1-(pyridin-2-yl)-3-(4-(trifluoromethyl)phenyl)-1H-pyrazol-5-ol,
3-(3-nitrophenyl)-1-(pyridin-2-yl)-1H-pyrazol-5-ol,
3-(4-nitrophenyl)-1-(pyridin-2-yl)-1H-pyrazol-5-ol,
3-(4-methoxyphenyl)-1-(pyridin-2-yl)-1H-pyrazol-5-ol,
3-(3,4-dimethoxyphenyl)-1-(pyridin-2-yl)-1H-pyrazol-5-ol, 1-(pyridin-2-yl)-3-(3,4,5-trimethoxyphenyl)-1H-pyrazol-5-ol,
3-(2-fluorophenyl)-1-(pyridin-2-yl)-1H-pyrazol-5-ol,
3-(3-fluorophenyl)-1-(pyridin-2-yl)-1H-pyrazol-5-ol,
3-(4-fluorophenyl)-1-(pyridin-2-yl)-1H-pyrazol-5-ol,
3-(2-chlorophenyl)-1-(pyridin-2-yl)-1H-pyrazol-5-ol,
3-(3-chlorophenyl)-1-(pyridin-2-yl)-1H-pyrazol-5-ol,
3-(4-chlorophenyl)-1-(pyridin-2-yl)-1H-pyrazol-5-ol,
3-(3-bromophenyl)-1-(pyridin-2-yl)-1H-pyrazol-5-ol,
3-(4-bromophenyl)-1-(pyridin-2-yl)-1H-pyrazol-5-ol,
3-(2-iodophenyl)-1-(pyridin-2-yl)-1H-pyrazol-5-ol,
3-(3-iodophenyl)-1-(pyridin-2-yl)-1H-pyrazol-5-ol,
3-(4-iodophenyl)-1-(pyridin-2-yl)-1H-pyrazol-5-ol,
3-(4-iodophenyl)-1-(pyrimidin-2-yl)-1H-pyrazol-5-ol,
2-(3-(4-iodophenyl)-5-(triisopropylsilyloxy)-1H-pyrazol-1-yl)pyridine,
3-(4-bromophenyl)-1-(pyridin-2-yl)-1H-pyrazol-5-yl tert-butyl carbonate,
tert-butyl 3-(2-iodophenyl)-1-(pyridin-2-yl)-1H-pyrazol-5-yl carbonate,
tert-butyl 3-(3-iodophenyl)-1-(pyridin-2-yl)-1H-pyrazol-5-yl carbonate,
tert-butyl 3-(4-iodophenyl)-1-(pyridin-2-yl)-1H-pyrazol-5-yl carbonate,
tert-butyl 3-(4-iodophenyl)-1-(pyrimidin-2-yl)-1H-pyrazol-5-yl carbonate,
3-(4-bromophenyl)-1-(pyridin-2-yl)-1H-pyrazol-5-yl acetate,
3-(biphenyl-4-yl)-1-(pyridin-2-yl)-1H-pyrazol-5-yl tert-butyl carbonate,
3-(4-(benzo[d][1,3]dioxol-5-yl)phenyl)-1-(pyridin-2-yl)-1H-pyrazol-5-yl tert-butyl carbonate,
3-(3'-phenylbiphenyl-4-yl)-1-(pyridin-2-yl)-1H-pyrazol-5-yl tert-butyl carbonate,
tert-butyl 3-(4-(naphthalene)phenyl)-1-(pyridin-2-yl)-1H-pyrazol-5-yl carbonate,
tert-butyl 3-(3'-(dimethylamino)biphenyl)-1-(pyridin-2-yl)-1H-pyrazol-5-yl carbonate,
3-(2-(benzo[d][1,3]dioxol-5-yl)phenyl)-1-(pyridin-2-yl)-1H-pyrazol-5-yl tert-butyl carbonate,
3-(3'-phenylbiphenyl-2-yl)-1-(pyridin-2-yl)-1H-pyrazol-5-yl tert-butyl carbonate,
3-(biphenyl-3-yl)-1-(pyridin-2-yl)-1H-pyrazol-5-yl tert-butyl carbonate,
3-(4'-(benzyloxy)biphenyl-3-yl)-1-(pyridin-2-yl)-1H-pyrazol-5-yl tert-butyl carbonate,
3-(4'-bromobiphenyl-3-yl)-1-(pyridin-2-yl)-1H-pyrazol-5-yl tert-butyl carbonate,
tert-butyl 3-(3'-formylbiphenyl-3-yl)-1-(pyridin-2-yl)-1H-pyrazol-5-yl carbonate,
tert-butyl 3-(2'-phenoxybiphenyl-3-yl)-1-(pyridin-2-yl)-1H-pyrazol-5-yl carbonate,
3-(3-(benzo[d][1,3]dioxol-5-yl)phenyl)-1-(pyridin-2-yl)-1H-pyrazol-5-yl tert-butyl carbonate,
3-(3'-phenylbiphenyl-3-yl)-1-(pyridin-2-yl)-1H-pyrazol-5-yl tert-butyl carbonate,
tert-butyl 3-(3-(naphthalen-1-yl)phenyl)-1-(pyridin-2-yl)-1H-pyrazol-5-yl carbonate,
tert-butyl 3-(3'-(dimethylamino)biphenyl-3-yl)-1-(pyridin-2-yl)-1H-pyrazol-5-yl carbonate,
tert-butyl 3-(4'-methoxybiphenyl-4-yl)-1-(pyridin-2-yl)-1H-pyrazol-5-yl carbonate,
3-(4'-(benzyloxy)biphenyl-4-yl)-1-(pyridin-2-yl)-1H-pyrazol-5-yl tert-butyl carbonate,
3-(4'-bromobiphenyl-4-yl)-1-(pyridin-2-yl)-1H-pyrazol-5-yl tert-butyl carbonate,
3-(3'-formylbiphenyl-4-yl)-1-(pyridin-2-yl)-1H-pyrazol-5-yl tert-butyl carbonate,
tert-butyl 3-(2'-phenoxybiphenyl-4-yl)-1-(pyridin-2-yl)-1H-pyrazol-5-yl carbonate,
3-(biphenyl-4-yl)-1-(pyrimidin-2-yl)-1H-pyrazol-5-yl tert-butyl carbonate,
3-(4-(benzo[d][1,3]dioxol-5-yl)phenyl)-1-(pyrimidin-2-yl)-1H-pyrazol-5-yl tert-butyl carbonate,
3-(3'-phenylbiphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(3'-phenylbiphenyl-4-yl)-1-(pyridin-2-yl)-1H-pyrazol-5-ol,
3-(4-(naphthalen-1-yl)phenyl)-1-(pyridin-2-yl)-1H-pyrazol-5-ol,
3-(3'-(dimethylamino)biphenyl-4-yl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(3'-phenylbiphenyl-2-yl)-1-(pyridin-2-yl)-1,1-pyrazol-5-ol,
3-(biphenyl-3-yl)-1-(pyridin-2-yl)-1H-pyrazol-5-ol,
3-(4'-(benzyloxy)biphenyl-3-yl)-1-(pyridin-2-yl)-1H-pyrazol-5-ol,
3-(4'-bromobiphenyl-3-yl)-1-(pyridin-2-yl)-1H-pyrazol-5-ol,
3-(3'-formylbiphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3-(benzo[d][1,3]dioxol-5-yl)phenyl)-1-(pyridin-2-yl)-1H-pyrazol-5-ol,
3-(3'-phenylbiphenyl-3-yl)-1-(pyridin-2-yl)-1H-pyrazol-5-ol,
3-(3-(naphthalen-1-yl)phenyl)-1-(pyridin-2-yl)-1H-pyrazol-5-ol,
3-(3'-(dimethylamino)biphenyl-3-yl)-1-(pyridin-2-yl)-1H-pyrazol-5-ol,
3-(4'-methoxybiphenyl-4-yl)-1-(pyridin-2-yl)-1H-pyrazol-5-ol,
3-(4'-(benzyloxy)biphenyl-4-yl)-1-(pyridin-2-yl)-1H-pyrazol-5-ol,
3-(4'-bromobiphenyl-4-yl)-1-(pyridin-2-yl)-1H-pyrazol-5-ol,
3-(3'-formylbiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol,
3-(biphenyl-4-yl)-1-(pyrimidin-2-yl)-1H-pyrazol-5-ol,
3-(4-(benzo[d][1,3]dioxol-5-yl)phenyl)-1-(pyrimidin-2-yl)-1H-pyrazol-5-ol,
3-(3'-phenylbiphenyl-4-yl)-1-(pyrimidin-2-yl)-1H-pyrazol-5-ol,
3-phenyl-4-propyl-1-(pyridin-2-yl)-1H-pyrazol-5-ol, and
4-benzyl-3-phenyl-1-(pyridin-2-yl)-1H-pyrazol-5-ol.

The composition of the present invention is preferably a composition for the prevention or treatment of osteoporosis, containing a compound or a pharmaceutically acceptable salt thereof selected from:
3-(4-bromophenyl)-1-(pyridin-2-yl)-1H-pyrazol-5-ol,
3-(2-iodophenyl)-1-(pyridin-2-yl)-1H-pyrazol-5-ol, 3-(3-iodophenyl)-1-(pyridin-2-yl)-1H-pyrazol-5-ol,
3-(4-iodophenyl)-1-(pyridin-2-yl)-1H-pyrazol-5-ol,
3-(4-iodophenyl)-1-(pyrimidin-2-yl)-1H-pyrazol-5-ol,
2-(3-(4-iodophenyl)-5-(triisopropylsilyloxy)-1H-pyrazol-1-yl)pyridine,
3-(4-bromophenyl)-1-(pyridin-2-yl)-1H-pyrazol-5-yl acetate,
3-(biphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(biphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3'-phenylbiphenyl-3-yl)-1-(pyridin-2-yl)-1H-pyrazol-5-ol,
3-(4'-bromobiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol,
3-(biphenyl-4-yl)-1-(pyrimidin-2-yl)-1H-pyrazol-5-ol,
3-phenyl-4-propyl-1-(pyridin-2-yl)-1H-pyrazol-5-ol, and
4-benzyl-3-phenyl-1-(pyridin-2-yl)-1H-pyrazol-5-ol.

As used herein, the term "osteoporosis" refers to a condition in which an absolute quantity of bone with exclusion of a vacant portion (such as marrow cavity) from the entire bone has been decreased, and is intended to encompass senile osteoporosis, post-menopausal osteoporosis, endocrine osteoporosis, congenital osteoporosis, immobilized osteoporosis and post-traumatic osteoporosis.

The composition containing the compound of formula I, the above-exemplified compound or a pharmaceutically acceptable salt thereof in accordance with the present invention is capable of preventing or treating osteoporosis by inhibiting the generation of reactive oxygen species. For example, the composition containing the compound of formula I, the above-exemplified compound or a pharmaceutically acceptable salt thereof in accordance with the present invention is capable of inhibiting the generation of reactive oxygen species by inhibiting NADPH oxidase. The composition of the present invention is capable of inhibiting the production of osteoclasts through the inhibition of NADPH oxidase which is an important substance for differentiation of macrophages into osteoclasts.

The composition containing the compound of formula I, the above-exemplified compound or a pharmaceutically acceptable salt thereof in accordance with the present invention is capable of treating or preventing osteoporosis through inhibition of osteoclast formation.

The pharmaceutical composition of the present invention may contain additives, such as a diluent, a binder, a disintegrant, a lubricant, a pH-adjusting agent, an antioxidant and a solubilizer, which are pharmaceutically acceptable, within the range where effects of the present invention are not impaired.

Examples of the diluent include sugar, starch, microcrystalline cellulose, lactose (lactose hydrate), glucose, D-mannitol, alginate, an alkaline earth metal salt, clay, polyethylene glycol, anhydrous dibasic calcium phosphate, and a mixture thereof; Examples of the binder include starch, microcrystalline cellulose, highly dispersive silica, mannitol, D-mannitol, sucrose, lactose hydrate, polyethylene glycol, polyvinylpyrrolidone (povidone), a polyvinylpyrrolidone copolymer (copovidone), hypromellose, hydroxypropylcellulose, natural gum, synthetic gum, copovidone, gelatin, and a mixture thereof.

Examples of the disintegrant include starches or modified starches such as sodium starch glycolate, corn starch, potato starch, and pregelatinized starch; clays such as bentonite, montmorillonite, and veegum; celluloses such as microcrystalline cellulose, hydroxypropylcellulose, and carboxymethylcellulose; algins such as sodium alginate, and alginic acid; crosslinked celluloses such as croscarmellose sodium; gums such as guar gum, and xanthan gum; crosslinked polymers such as crosslinked polyvinylpyrrolidone (crospovidone); effervescent agents such as sodium bicarbonate and citric acid, and mixtures thereof.

Examples of the lubricant include talc, stearic acid, magnesium stearate, calcium stearate, sodium lauryl sulfate, hydrogenated vegetable oil, sodium benzoate, sodium stearyl fumarate, glyceryl behenate, glyceryl monolaurate, glyceryl monostearate, glyceryl palmitostearate, colloidal silicon dioxide, and mixtures thereof.

Examples of the pH-adjusting agent include acidifying agents such as acetic acid, adipic acid, ascorbic acid, sodium ascorbate, sodium etherate, malic acid, succinic acid, tartaric acid, fumaric acid, and citric acid, and basifying agents such as precipitated calcium carbonate, aqueous ammonia, meglumine, sodium carbonate, magnesium oxide, magnesium carbonate, sodium citrate, and tribasic calcium phosphate.

Examples of the antioxidant include dibutyl hydroxy toluene, butylated hydroxyanisole, tocopherol acetate, tocopherol, propyl gallate, sodium hydrogen sulfite, and sodium pyrosulfite. Examples of the solubilizer that can be used in the immediate-release compartment of the present invention include sodium lauryl sulfate, polyoxyethylene sorbitan fatty acid ester (such as polysorbate), docusate sodium and poloxamer.

In order to prepare a delayed-release formulation, the pharmaceutical composition of the present invention may contain an enteric polymer, a water-insoluble polymer, a hydrophobic compound, and a hydrophilic polymer.

The enteric polymer refers to a polymer which is insoluble or stable under acidic conditions of less than pH 5 and is dissolved or degraded under specific pH conditions of pH 5 or higher. Examples of the enteric polymer include enteric cellulose derivatives such as hypromellose acetate succinate, hypromellose phthalate (hydroxypropylmethylcellulose phthalate), hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate, and methylhydroxyethylcellulose; enteric acrylic acid copolymers such as a styrene/acrylic acid copolymer, a methyl acrylate/acrylic acid copolymer, a methyl acrylate/methacrylic acid copolymer (e.g., Acryl-EZE), a butyl acrylate/styrene/acrylic acid copolymer, and a methyl acrylate/methacrylic acid/octyl acrylate copolymer; enteric polymethacrylate copolymers such as a poly(methacrylic acid/methyl methacrylate) copolymer (e.g., Eudragit L or Eudragit S, manufactured by Evonik, Germany), and a poly(methacrylic acid/ethyl acrylate) copolymer (e.g., Eudragit L100-55, manufactured by Evonik, Germany); enteric maleic acid copolymers such as a vinyl acetate/maleic anhydride copolymer, a styrene/maleic anhydride copolymer, a styrene/maleic monoester copolymer, a vinyl methyl ether/maleic anhydride copolymer, an ethylene/maleic anhydride copolymer, a vinyl butyl ether/maleic anhydride copolymer, an acrylonitrile/methyl acrylate/maleic anhydride copolymer, and a butyl acrylate/styrene/maleic anhydride copolymer; and enteric polyvinyl derivatives such as polyvinyl alcohol phthalate, polyvinylacetal phthalate, polyvinylbutyrate phthalate, and polyvinylacetacetal phthalate.

The water-insoluble polymer refers to a pharmaceutically acceptable water-insoluble polymer which controls the release of a drug. Examples of the water-insoluble polymer include polyvinyl acetate (e.g. Kollicoat SR30D), a water-insoluble polymethacrylate copolymer {e.g. poly(ethyl acrylate-methyl methacrylate) copolymer (such as Eudragit NE30D, a poly(ethyl acrylate-methyl methacrylate-trimethylaminoethyl methacrylate) copolymer (e.g. Eudragit RSPO)}, ethylcellulose, cellulose ester, cellulose ether, cellulose acylate, cellulose diacylate, cellulose triacylate, cellulose acetate, cellulose diacetate, and cellulose triacetate.

The hydrophobic compound refers to a pharmaceutically acceptable water-insoluble material which controls the release of a drug. Examples of the hydrophobic compound include fatty acids and fatty acid esters such as glyceryl palmitostearate, glyceryl stearate, glyceryl behenate, cetyl palmitate, glyceryl monooleate and stearic acid; fatty acid alcohols such as cetostearyl alcohol, cetyl alcohol and stearyl alcohol; waxes such as carnauba wax, beeswax and microcrystalline wax; and inorganic materials such as talc, precipitated calcium carbonate, calcium hydrogen phosphate, zinc oxide, titanium oxide, kaolin, bentonite, montmorillonite and veegum.

The hydrophilic polymer refers to a pharmaceutically acceptable water-soluble polymer which controls the release of a drug. Examples of the hydrophilic polymer include saccharides such as dextrin, polydextrin, dextran, pectin and a pectin derivative, alginate, polygalacturonic acid, xylan, arabinoxylan, arabinogalactan, starch, hydroxypropyl starch, amylose and amylopectin; cellulose derivatives such as hypromellose, hydroxypropylcellulose, hydroxymethylcellulose, hydroxyethylcellulose, methylcellulose, and sodium carboxymethylcellulose; gums such as guar gum, locust bean gum, tragacanth, carrageenan, gum acacia, gum arabic, gellan gum and xanthan gum; proteins such as gelatin, casein and zein; polyvinyl derivatives such as polyvinyl alcohol, polyvinylpyrrolidone and polyvinylacetal diethylaminoacetate; hydrophilic polymethacrylate copolymers such as a poly(butyl methacrylate-(2-dimethylaminoethyl)methacrylate-methyl methacrylate) copolymer (e.g. Eudragit E100, manufactured by Evonik, Germany), and a poly(ethyl acrylate-methyl methacrylate-triethylaminoethyl-methacrylate chloride) copolymer (e.g. Eudragit RL and RS, manufactured by Evonik, Germany); polyethylene derivatives such as polyethylene glycol and polyethylene oxide; and carbomer.

In addition, the composition of the present invention may optionally contain pharmaceutically acceptable additives such as various additives selected from colorants and fragrances.

The range of the additive that can be used in the present invention is not limited to the above-mentioned additives, and the additive may be used in a conventional dose which can be appropriately selected by those skilled in the art.

The pharmaceutical composition in accordance with the present invention may be formulated into an oral dosage form such as a powder, a granule, a tablet, a capsule, a suspension, an emulsion, a syrup or an aerosol, or a parenteral dosage form such as an agent for external use, a suppository or a sterile injection, according to a conventional known method.

Further, the present invention provides a method for preventing or treating osteoporosis, including administering the compound of formula I, the above-exemplified compound or a pharmaceutically acceptable salt thereof in accordance with the present invention to a subject including a mammal. As used herein, the term "administering" means the introduction of the composition for the prevention or treatment of osteoporosis in accordance with the present invention to a patient via any appropriate method. The composition for the prevention or treatment of osteoporosis in accordance with the present invention may be administered via any conventional administration route as long as the composition can reach a target tissue. For example, the composition may be administered orally, intraperitoneally, intravenously, intramuscularly, subcutaneously, intradermally, intranasally, intrapulmonary, rectally, intracavitally or intrathecally without being limited thereto.

The composition for the prevention or treatment of osteoporosis in accordance with the present invention may be administered once a day or may be administered at regular time intervals twice or more a day.

The dosage of the compound of formula I in accordance with the present invention varies depending on body weight, age, gender, and health state of the patient, diet, administration timing, administration route, excretion rate, and severity of the disease. The compound of formula I is administered at a dose of 0.1 to 100 mg/kg/day and preferably at a dose of 10 to 40 mg/kg/day, but may vary depending on sex and age of the patient, severity of the disease, or the like.

Further, the present invention provides a method for inhibiting the generation of reactive oxygen species, including administering the compound of formula I, the above-exemplified compound or a pharmaceutically acceptable salt thereof in accordance with the present invention to a subject including a mammal.

Further, the present invention provides a method for inhibiting the production of osteoclasts, including administering the compound of formula I, the above-exemplified compound or a pharmaceutically acceptable salt thereof in accordance with the present invention to a subject including a mammal.

Further, the present invention provides use of the compound of formula I, the above-exemplified compound or a pharmaceutically acceptable salt thereof in accordance with the present invention, for the preparation of a pharmaceutical formulation for the treatment or prevention of osteoporosis.

Further, the present invention provides a health food containing the compound of formula I, the above-exemplified compound or a pharmaceutically acceptable salt thereof in accordance with the present invention. Preferred is a health food for strengthening bone.

Further, the present invention provides a reactive oxygen species-generating inhibitor for inhibiting the generation of reactive oxygen species, containing the compound of formula I, the above-exemplified compound or a pharmaceutically acceptable salt thereof.

Advantageous Effects

The compound of the present invention has excellent inhibitory activity on the generation of reactive oxygen species and may also be used for the treatment or prevention of osteoporosis without adverse side effects as exhibited by conventional therapeutic agents.

MODE FOR INVENTION

Figure 1:
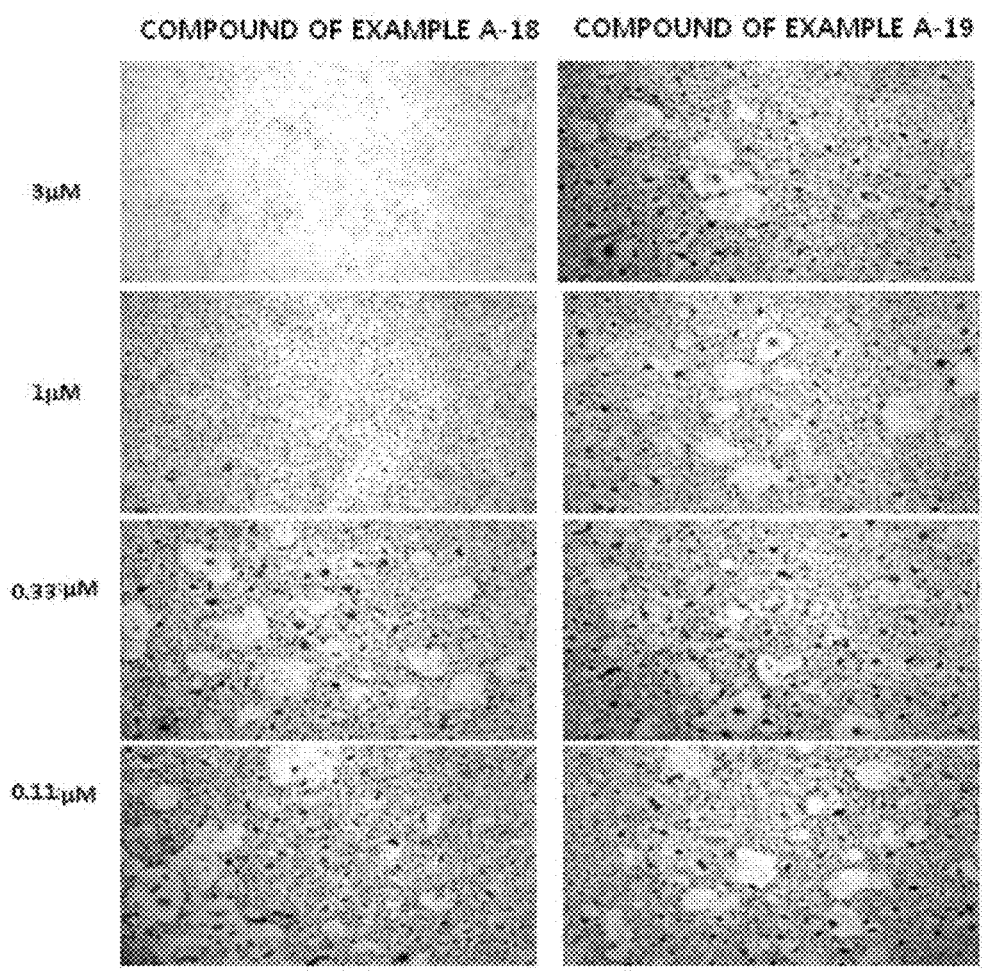
FIGS. 1 to 4 are a view showing an inhibitory effect of compounds of the present invention on osteoclastic differentiation.

Hereinafter, the present invention will be described in more detail with reference to the following Examples and Experimental Examples. However, it should be understood that the following Examples are provided only for illustrating the present invention and should not be construed as limiting the scope and spirit of the present invention.

A. Synthesis of Compound of Formula I-1

Example A-1

Synthesis of 1-(pyridin-2-yl)-3-(3-(trifluoromethyl)phenyl)-1H-pyrazol-5-ol (1)

Ethyl 3-trifluoromethylbenzoylacetate (10 mmol, manufactured by Aldrich) and ethanol (10 mL) were charged in a 100 mL round-bottom flask to which a solution of 2-hydrazinopyridine (10 mmol, manufactured by Aldrich) in ethanol (10 mL) was then added.

After being stirred at 100° C. for 8 hours, the reaction liquid was cooled at room temperature. The resulting solid was filtered, washed with ethanol and hexane, and then dried under vacuum to afford the title compound.

$^1$H NMR (300 MHz, CDCl$_3$) δ 12.8 (br, 1H), 8.30 (s, 1H), 8.14 (s, 1H), 8.08-7.93 (m, 3H), 7.59-7.53 (m, 2H), 7.20 (s, 1H), 5.97 (s, 1H).

EIMS (70 eV) m/z (rel intensity); 306 (27), 305 (M+, 100), 277 (15), 264 (35), 170 (11), 160 (27), 150 (12), 93 (13), 79 (88), 77 (30), 66 (8), 52 (17).

Example A-2

Synthesis of 1-(pyridin-2-yl)-3-(4-(trifluoromethyl)phenyl)-1H-pyrazol-5-ol (2)

The title compound was synthesized in the same manner as in Example A-1, except that an equimolar amount of ethyl 4-trifluoromethylbenzoylacetate (manufactured by Aldrich) was used in place of ethyl 3-trifluoromethylbenzoylacetate.

$^1$H NMR (300 MHz, CDCl$_3$) δ 12.8 (br, 1H), 8.31-8.29 (m, 1H), 8.06 (d, 1H, J=8.4 Hz), 7.97-7.89 (m, 3H), 7.67 (d, 2H, J=8.2 Hz), 7.23-7.18 (m, 1H), 5.98 (s, 1H).

EIMS (70 eV) m/z (rel intensity); 306 (18), 305 (M+, 100), 304 (10), 264 (19), 160 (18) 151 (10), 79 (71), 78 (24), 52 (14).

Example A-3

Synthesis of 3-(3-nitrophenyl)-1-(pyridin-2-yl)-1H-pyrazol-5-ol (3)

The title compound was synthesized in the same manner as in Example A-1, except that an equimolar amount of ethyl 3-nitrobenzoylacetate (manufactured by Aldrich) was used in place of ethyl 3-trifluoromethylbenzoylacetate.

$^1$H NMR (300 MHz, CDCl$_3$) δ 12.8 (br, 1H), 8.72 (s, 1H), 8.32 (d, 1H, J=4.5 Hz), 8.21-8.14 (m, 2H), 8.09 (d, 1H, J=8.3 Hz), 7.96 (t, 1H, J=4.5 Hz), 7.59 (t, 1H, J=7.9 Hz), 7.23 (d, 1H, J=6.2 Hz), 6.01 (s, 1H).

EIMS (70 eV) m/z (rel intensity) 282 (M+, 100), 254 (7), 241 (11), 236 (4), 195 (7), 101 (13), 79 (59), 78 (30).

Example A-4

Synthesis of 3-(4-nitrophenyl)-1-(pyridin-2-yl)-1H-pyrazol-5-ol (4)

The title compound was synthesized in the same manner as in Example A-1, except that an equimolar amount of ethyl 4-nitrobenzoylacetate (manufactured by Aldrich) was used in place of ethyl 3-trifluoromethylbenzoylacetate.

$^1$H NMR (300 MHz, CDCl$_3$) δ 12.8 (br, 1H), 8.33-8.26 (m, 3H), 8.08-7.92 (m, 4H), 7.25-7.22 (m, 1H), 6.01 (s, 1H).

EIMS (70 eV) m/z (rel intensity) 282 (M+, 100), 241 (10), 236 (12) 208 (13), 195 (8), 160 (11), 150 (6), 101 (9), 79 (53), 78 (31), 75 (9).

Example A-5

Synthesis of 3-(4-methoxyphenyl)-1-(pyridin-2-yl)-1H-pyrazol-5-ol (5)

The title compound was synthesized in the same manner as in Example A-1, except that an equimolar amount of ethyl 4-methoxybenzoylacetate (manufactured by Aldrich) was used in place of ethyl 3-trifluoromethylbenzoylacetate.

$^1$H NMR (300 MHz, CDCl$_3$) δ 12.8 (br, 1H), 8.26 (d, 1H, J=5.1 Hz), 8.02 (d, 1H, J=8.4 Hz), 7.88 (t, 1H, J=8.3 Hz), 7.79 (d, 2H, J=8.8 Hz), 7.14 (t, 1H, J=6.3 Hz), 6.95 (d, 2H, J=8.8 Hz), 5.87 (s, 1H), 3.84 (s, 3H).

EIMS (70 eV) m/z (rel intensity) 267 (M+, 100), 226 (15), 145 (4), 133 (19), 117 (7), 89 (10) 79 (28).

Example A-6

Synthesis of 3-(3,4-dimethoxyphenyl)-1-(pyridin-2-yl)-1H-pyrazol-5-ol (6)

The title compound was synthesized in the same manner as in Example A-1, except that an equimolar amount of ethyl 3,4-dimethoxybenzoylacetate (manufactured by Aldrich) was used in place of ethyl 3-trifluoromethylbenzoylacetate.

$^1$H NMR (300 MHz, CDCl$_3$) δ 12.8 (br, 1H), 8.29 (d, 1H, J=4.3 Hz), 8.05 (d, 1H, J=8.0 Hz), 7.91 (t, 1H, J=7.4 Hz), 7.47 (s, 1H), 7.36 (d, 1H, J=8.3 Hz), 7.17 (t 1H, J=6.2 Hz), 6.92 (d, 1H, J=8.2 HZ), 5.89 (s, 1H), 3.96 (d, 6H, J=18.1 Hz).

EIMS (70 eV) m/z (rel intensity) 297 (M+, 100), 298 (23), 282 (13), 269 (2), 163 (10), 121 (23), 79 (21).

Example A-7

Synthesis of 1-(pyridin-2-yl)-3-(3,4,5-trimethoxyphenyl)-1H-pyrazol-5-ol (7)

The title compound was synthesized in the same manner as in Example A-1, except that an equimolar amount of ethyl 3,4,5-trimethoxybenzoylacetate (manufactured by Aldrich) was used in place of ethyl 3-trifluoromethylbenzoylacetate.

$^1$H NMR (300 MHz, CDCl$_3$) δ 12.8 (br, 1H), 8.29 (d, 1H, J=4.8 Hz), 7.94-7.88 (m, 1H), 7.18 (t, 1H, J=6.5 Hz), 7.08 (s, 1H), 5.90 (s, 1H), 3.95 (s, 6H), 3.88 (s, 3H).

Example A-8

Synthesis of 3-(2-fluorophenyl)-1-(pyridin-2-yl)-1H-pyrazol-5-ol (8)

The title compound was synthesized in the same manner as in Example A-1, except that an equimolar amount of ethyl 2-fluorobenzoylacetate (manufactured by Aldrich) was used in place of ethyl 3-trifluoromethylbenzoylacetate.
$^1$H NMR (300 MHz, CDCl$_3$) δ 12.7 (br, 1H), 8.33 (s, 1H), 8.15-8.07 (m, 2H), 7.97-7.91 (m, 1H), 7.39-7.29 (m, 2H), 7.25-7.13 (m, 2H), 6.14 (s, 1H).
EIMS (70 eV) m/z (rel intensity) 256 (48), 255 (M+, 100), 254 (81), 235 (49), 227 (32), 214 (75), 207 (51), 198 (18), 180 (14), 170 (3), 159 (34), 146 (16), 128 (33), 119 (58), 113 (11), 106 (19), 100 (39), 93 (16), 79 (96), 66 (11), 57 (7), 52 (34).

Example A-9

Synthesis of 3-(3-fluorophenyl)-1-(pyridin-2-yl)-1H-pyrazol-5-ol (9)

The title compound was synthesized in the same manner as in Example A-1, except that an equimolar amount of ethyl 3-fluorobenzoylacetate (manufactured by Aldrich) was used in place of ethyl 3-trifluoromethylbenzoylacetate.
$^1$H NMR (300 MHz, CDCl$_3$) δ 12.8 (br, 1H), 8.33 (s, 1H), 8.10-7.92 (m, 2H), 7.65-7.61 (m, 2H), 7.45-7.38 (m, 1H), 7.29-7.28 (m, 0.5H), 7.25-7.21 (m, 0.5H), 7.10-7.05 (m, 1H), 5.96 (s, 1H).
EIMS (70 eV) m/z (rel intensity); 256 (31), 255 (M+, 100), 227 (20), 214 (47), 198 (13), 160 (30), 146 (10), 133 (12), 121 (22) 119 (34), 106 (12), 79 (88), 52 (24).

Example A-10

Synthesis of 3-(4-fluorophenyl)-1-(pyridin-2-yl)-1H-pyrazol-5-ol (10)

The title compound was synthesized in the same manner as in Example A-1, except that an equimolar amount of ethyl 4-fluorobenzoylacetate (manufactured by Aldrich) was used in place of ethyl 3-trifluoromethylbenzoylacetate.
$^1$H NMR (300 MHz, CDCl$_3$) δ 12.8 (br, 1H), 8.30 (d, 1H, J=5.1 Hz), 8.03 (d, 1H, J=8.4 Hz), 7.93-7.81 (m, 3H), 7.20-7.07 (m, 3H), 5.89 (s, 1H).
EIMS (70 eV) m/z (rel intensity); 256 (21), 255 (M+, 100), 227 (12), 214 (33), 160 (12), 134 (10), 121 (20), 120 (25), 93 (11), 79 (75), 78 (23).

Example A-11

Synthesis of 3-(2-chlorophenyl)-1-(pyridin-2-yl)-1H-pyrazol-5-ol (11)

The title compound was synthesized in the same manner as in Example A-1, except that an equimolar amount of ethyl 2-chlorobenzoylacetate (manufactured by Aldrich) was used in place of ethyl 3-trifluoromethylbenzoylacetate.
$^1$H NMR (300 MHz, CDCl$_3$) δ 12.7 (br, 1H), 8.31-8.29 (m, 1H), 8.03 (d, 1H, J=8.2 Hz), 7.93-7.83 (m, 2H), 7.47-7.44 (m, 1H), 7.36-7.29 (m, 2H), 7.21-7.17 (m, 1H), 6.14 (s, 1H).
EIMS (70 eV) m/z (rel intensity) 271 (M+, 100), 236 (48), 230 (16), 208 (22), 181 (13), 160 (15), 135 (27), 100 (24), 79 (87), 78 (38), 75 (17), 66 (10), 52 (27), 51 (16).

Example A-12

Synthesis of 3-(3-chlorophenyl)-1-(pyridin-2-yl)-1H-pyrazol-5-ol (12)

The title compound was synthesized in the same manner as in Example A-1, except that an equimolar amount of ethyl 3-chlorobenzoylacetate (manufactured by Aldrich) was used in place of ethyl 3-trifluoromethylbenzoylacetate.
$^1$H NMR (300 MHz, CDCl$_3$) δ 12.8 (br, 1H), 8.30-8.28 (m, 1H), 8.05 (d, 1H, J=8.5 Hz), 7.94-7.88 (m, 2H), 7.72-7.69 (m, 1H), 7.37-7.30 (m, 2H), 7.20 (t, 1H, J=6.3 Hz), 5.92 (s, 1H).
EIMS (70 eV) m/z (rel intensity) 273 (76), 271 (M+, 100), 270 (69), 243 (28), 230 (60), 160 (40), 135 (30), 100 (13), 93 (11), 79 (60), 77 (22), 52 (14).

Example A-13

Synthesis of 3-(4-chlorophenyl)-1-(pyridin-2-yl)-1H-pyrazol-5-ol (13)

The title compound was synthesized in the same manner as in Example A-1, except that an equimolar amount of ethyl 4-chlorobenzoylacetate (manufactured by Aldrich) was used in place of ethyl 3-trifluoromethylbenzoylacetate.
$^1$H NMR (300 MHz, CDCl$_3$) δ 12.7 (br, 1H), 8.28 (br, 1H), 8.03 (d, 1H, J=8.1 Hz), 7.93-7.88 (m, 1H), 7.79 (d, 2H, J=7.9 Hz), 7.39 (d, 211, J=8.0 Hz), 7.18-7.17 (m, 1H), 5.91 (s, 1H).
EIMS (70 eV) m/z (rel intensity) 274 (22), 272 (71), 271 (M+, 100), 243 (30), 230 (67), 214 (12), 207 (5), 194 (1), 179 (4), 160 (30), 149 (8), 135 (43), 121 (13), 110 (7), 100 (16), 93 (12), 79(69), 66 (5).

Example A-14

Synthesis of 3-(3-bromophenyl)-1-(pyridin-2-yl)-1H-pyrazol-5-ol (14)

The title compound was synthesized in the same manner as in Example A-1, except that an equimolar amount of ethyl 3-bromobenzoylacetate (manufactured by Aldrich) was used in place of ethyl 3-trifluoromethylbenzoylacetate.
$^1$H NMR (300 MHz, CDCl$_3$) δ 12.8 (br, 1H), 8.30 (d, 1H, J=5.8 Hz), 8.07-8.04 (m, 2H), 7.95-7.89 (m, 1H), 7.76 (d, 1H, J=8.1 Hz), 7.48 (d, 1H, J=8.0 Hz), 7.31-7.28 (m, 1H), 7.22-7.18 (m, 1H), 5.92 (s, 1H).
EIMS (70 eV) m/z (rel intensity); 318 (15), 316 (M+, 99), 315 (99), 275 (16), 273 (20), 207 (10), 181 (11), 179 (10), 160 (34), 118 (25), 101 (34), 93 (13), 79 (100), 77 (33), 75 (20), 52 (23), 51 (13).

Example A-15

Synthesis of 3-(4-bromophenyl)-1-(pyridin-2-yl)-1H-pyrazol-5-ol (15)

The title compound was synthesized in the same manner as in Example A-1, except that an equimolar amount of ethyl 4-bromobenzoylacetate (manufactured by Aldrich) was used in place of ethyl 3-trifluoromethylbenzoylacetate.
Yield: 81% (2.5 g, 8.0 mmol)
$^1$H NMR (300 MHz, CDCl$_3$) δ 12.8 (br, 1H) 8.30-8.28 (m, 1H), 8.03 (d, 1H, J=8.5 Hz), 7.94-7.88 (m, 1H), 7.73 (d, 2H, J=8.6 Hz), 7.54 (d, 2H, J=8.6 Hz), 7.21-7.16 (m, 1H), 5.91 (s, 1H);
EIMS (70 eV) m/z (rel intensity) 315 (M+, 25), 317 (M+, 26), 101 (19), 79 (100).

Example A-16

Synthesis of 3-(2-iodophenyl)-1-(pyridin-2-yl)-1H-pyrazol-5-ol (16)

The title compound was synthesized in the same manner as in Example A-1, except that an equimolar amount of ethyl 2-iodobenzoylacetate (manufactured by Aldrich) was used in place of ethyl 3-trifluoromethylbenzoylacetate.

Yield: 46.8%

$^1$H NMR (300 MHz, CDCl$_3$) δ 12.81 (br, 1H) 8.33-8.30 (m, 1H), 8.05-7.97 (m, 2H), 7.93-7.87 (m, 1H), 7.61-7.58 (m, 1H) 7.44-7.38 (m, 1H), 7.23-7.18 (m, 1H), 7.10-7.04 (m, 1H), 5.99 (s, 1H).

Example A-17

Synthesis of 3-(3-iodophenyl)-1-(pyridin-2-yl)-1H-pyrazol-5-ol (17)

The title compound was synthesized in the same manner as in Example A-1, except that an equimolar amount of ethyl 3-iodobenzoylacetate (manufactured by Aldrich) was used in place of ethyl 3-trifluoromethylbenzoylacetate.

Yield: 80.4%

$^1$H NMR (300 MHz, CDCl$_3$) δ 12.84 (br, 1H) 8.31-8.29 (m, 1H), 8.25-8.24 (m, 1H), 8.08-8.04 (m, 1H), 7.95-7.89 (m, 1H), 7.81-7.77 (m, 1H), 7.70-7.66 (m, 1H), 7.23-7.13 (m, 2H), 5.91 (s, 1H).

Example A-18

Synthesis of 3-(4-iodophenyl)-1-(pyridin-2-yl)-1H-pyrazol-5-ol (18)

The title compound was synthesized in the same manner as in Example A-1, except that an equimolar amount of ethyl 4-iodobenzoylacetate (manufactured by Aldrich) was used in place of ethyl 3-trifluoromethylbenzoylacetate.

Yield: 65.0%

$^1$H NMR (300 MHz, CDCl$_3$) δ 12.76 (br, 1H) 8.30-8.27 (m, 1H), 8.05-8.01 (m, 1H), 7.93-7.87 (m, 1H), 7.78-7.72 (m, 2H), 7.62-7.57 (m, 2H), 7.20-7.16 (m, 1H), 5.91 (s, 1H);

EIMS m/z (rel intensity) 363 (M+, 100), 364 (33), 321 (20), 100 (27), 79 (85).

Example A-19

Synthesis of 3-(4-iodophenyl)-1-(pyrimidin-2-yl)-1H-pyrazol-5-ol (19)

Ethyl 4-iodobenzoylacetate (10 mmol, manufactured by Aldrich) and ethanol (10 mL) were charged in a 100 mL round-bottom flask to which a solution of 2-hydrazinopyrimidine (10 mmol, manufactured by Aldrich) in ethanol (10 mL) was then added. After being stirred at 100° C. for 8 hours, the reaction liquid was cooled at room temperature. The resulting solid was filtered, washed with ethanol and hexane, and then dried under vacuum to afford the title compound.

Yield: 49%

$^1$H NMR (300 MHz, CDCl$_3$) δ 11.94-11.92 (bs, 1H), 8.79 (d, 2H, J=4.9 Hz), 7.77-7.73 (m, 2H), 7.69-7.65 (m, 2H), 7.27-7.23 (m, 1H), 5.98 (s, 1H)

B. Synthesis of Compound of Formula I-2

Example B-1

Synthesis of 2-(3-(4-iodophenyl)-5-(triisoropylsilyloxy)-1H-pyrazol-1-yl)pyridine (20)

3-(4-iodophenyl)-1-(pyridin-2-yl)-1H-pyrazol-5-ol (0.5 mmol, 1 equivalent) was dissolved in CH$_2$Cl$_2$ (5 mL) to which 3 equivalents of triethylamine were then added. Under stream of nitrogen, 2 equivalents of triisopropylsilyl chloride (TIP-SCl) were added thereto at 0° C., followed by stirring at room temperature. After 10 minutes, the solution was concentrated by distillation under reduced pressure and hexane was added thereto, followed by washing with a saturated NaHCO$_3$ aqueous solution. After extraction with hexane twice, the organic layer was dried over anhydrous MgSO$_4$, filtered, concentrated and then dried under vacuum to afford the title compound.

Yield: 98%

$^1$H NMR (300 MHz, CDCl$_3$) δ 8.59-8.57 (m, 1H), 7.82-7.77 (m, 1H), 7.72 (d, 2H, J=8.5 Hz), 7.69-7.68 (m, 1H), 7.61 (d, 2H, J=8.6 Hz), 7.25-7.21 (m, 1H), 5.9 (s, 1H), 1.37-1.19 (m, 3H), 1.10-1.05 (m, 18H)

Example B-2

Synthesis of 3-(4-bromophenyl)-1-(pyridin-2-yl)-1H-pyrazol-5-yl tert-butyl carbonate (21)

2 mmol of 3-(4-bromophenyl)-1-(pyridin-2-yl)-1H-pyrazol-5-ol (15) prepared in Example A-15 was dissolved in methylene chloride (10 mL) to which 4-dimethylaminopyridine (DMAP, 0.05 equivalents) was then added. Thereafter, di-tert-butyl dicarbonate (2.2 equivalents) was added thereto, followed by stirring at room temperature for 30 minutes. After completion of the reaction was confirmed by TLC, the reaction liquid was washed three times with water. The organic layer was dried over anhydrous MgSO$_4$, filtered and concentrated to afford the title compound as a white solid.

Yield: 98%

$^1$H NMR (300 MHz, CDCl$_3$) δ 8.43-8.41 (m, 1H), 7.98 (d, 1H, J=8.3 Hz), 7.85-7.80 (m, 1H), 7.75 (d, 2H, J=8.5 Hz), 7.55 (d, 2H, J=8.6 Hz), 7.22-7.18 (m, 1H), 6.49 (s, 1H), 1.57 (s, 9H)

Example B-3

Synthesis of tert-butyl 3-(2-iodophenyl)-1-(pyridin-2-yl)-1H-pyrazol-5-yl carbonate (22)

The title compound was prepared in the same manner as in Example B-2, except that an equimolar amount of 3-(2-iodophenyl)-1-(pyridin-2-yl)-1H-pyrazol-5-ol (16) prepared in Example A-16 was used in place of 3-(4-bromophenyl)-1-(pyridin-2-yl)-1H-pyrazol-5-ol (15).

Yield: 97%

$^1$H NMR (300 MHz, CDCl$_3$) δ 8.42-8.41 (m, 1H), 7.97 (d, 2H, J=8.1 Hz), 7.83-7.78 (m, 1H), 7.63 (d, 1H, J=7.6 Hz), 7.43-7.38 (m, 1H), 7.21-7.17 (m, 1H), 7.08-7.03 (m, 1H), 6.59 (s, 1H), 1.57 (s, 9H)

Example B-4

Synthesis of tert-butyl 3-(3-iodophenyl)-1-(pyridin-2-yl)-1H-pyrazol-5-yl carbonate (23)

The title compound was prepared in the same manner as in Example B-2, except that an equimolar amount of 3-(3-iodophenyl)-1-(pyridin-2-yl)-1H-pyrazol-5-ol (17) prepared in Example A-17 was used in place of 3-(4-bromophenyl)-1-(pyridin-2-yl)-1H-pyrazol-5-ol (15).

Yield: 99%

$^1$H NMR (300 MHz, CDCl$_3$) δ 8.43-8.41 (m, 1H), 8.26-8.25 (m, 1H), 8.01-7.98 (m, 1H), 7.86-7.78 (m, 2H), 7.70-7.66 (m, 1H), 7.23-7.13 (m, 2H), 6.50 (s, 1H), 1.57 (s, 9H)

Example B-5

Synthesis of tert-butyl 3-(4-iodophenyl)-1-(pyridin-2-yl)-1H-pyrazol-5-yl carbonate (24)

The title compound was prepared in the same manner as in Example B-2, except that an equimolar amount of 3-(4-iodophenyl)-1-(pyridin-2-yl)-1H-pyrazol-5-ol (18) prepared in Example A-18 was used in place of 3-(4-bromophenyl)-1-(pyridin-2-yl)-1H-pyrazol-5-ol (15).

Yield: 99%

$^1$H NMR (300 MHz, CDCl$_3$) δ 8.42-8.40 (m, 1H), 7.98 (d, 1H, J=8.3 Hz), 7.85-7.80 (m, 1H), 7.76 (d, 2H, J=8.5 Hz), 7.61 (d, 2H, J=8.5 Hz), 7.22-7.18 (m, 1H), 6.5 (s, 1H), 1.57 (s, 9H)

Example B-6

Synthesis of tert-butyl 3-(4-iodophenyl)-1-(pyrimidin-2-yl)-1H-pyrazol-5-yl carbonate (25)

The title compound was prepared in the same manner as in Example B-2, except that an equimolar amount of 3-(4-iodophenyl)-1-(pyrimidin-2-yl)-1H-pyrazol-5-ol (19) prepared in Example A-19 was used in place of 3-(4-bromophenyl)-1-(pyridin-2-yl)-1H-pyrazol-5-ol (15).

Yield: 99%

$^1$H NMR (300 MHz, CDCl$_3$) δ 8.79 (d, 2H, J=4.8 Hz), 7.76 (d, 2H, J=8.3 Hz), 7.67 (d, 2H, J=8.3 Hz), 7.26-7.22 (m, 1H), 6.54 (s, 1H), 1.58 (s, 9H)

Example B-7

Synthesis of 3-(4-bromophenyl)-1-(pyridin-2-yl)-1H-pyrazol-5-yl acetate (26)

3-(4-bromophenyl)-1-(pyridin-2-yl)-1H-pyrazol-5-ol (3 mmol, 1 equivalent) was dissolved in 10 mL of CHCl$_3$ and 1.2 equivalents of triethylamine were added thereto at 0° C. Then, 1 equivalent of acetyl chloride was added thereto, followed by refluxing for 10 minutes. After the reaction was completed, H$_2$O (10 mL) was added to the solution which was then extracted with CHCl$_3$. The organic layer was dried over anhydrous MgSO$_4$, filtered, concentrated, and then separated by column chromatography (n-hexane:EA=5:1 (v/v)) to afford the title compound.

C. Synthesis of Compound of Formula I-3

Example C-1

Synthesis of 3-(biphenyl-4-yl)-1-(pyridin-2-yl)-1H-pyrazol-5-yl tert-butyl carbonate (27)

1 mmol of 3-(4-bromophenyl)-1-(pyridin-2-yl)-1H-pyrazol-5-yl tert-butyl carbonate (21) prepared in Example B-2 was charged in a 50 mL round-bottom flask and dissolved in 1,4-dioxane (10 mL), and phenylboronic acid (2.5 equivalents, manufactured by Aldrich) and K$_3$PO$_4$ (3 equivalents) were added thereto. Thereafter, PdCl$_2$(dppf) (0.08 equivalents, manufactured by Aldrich) and dppf (1,1'-bis(diphenylphosphino)ferrocene, 0.04 equivalents, manufactured by Aldrich) were added thereto, followed by heating at 100° C. for 10 minutes. After the solid was filtered through Celite, the organic layer was concentrated under reduced pressure, dissolved in ethyl acetate and then washed with water. The organic layer was dried over anhydrous MgSO$_4$ and concentrated. The resulting residue was purified by column chromatography (n-hexane:EA (ethyl acetate)=5:1 (v/v)) to afford the title compound.

Yield: 90.5%

$^1$H NMR (300 MHz, CDCl$_3$) δ 8.44-8.41 (m, 1H), 8.05-8.02 (m, 1H), 7.97-7.93 (m, 2H), 7.87-7.81 (m, 1H), 7.69-7.64 (m, 4H), 7.49-7.44 (m, 2H), 7.39-7.34 (m, 1H), 7.22-7.18 (m, 1H), 6.56 (s, 1H), 1.58 (s, 9H).

Example C-2

Synthesis of 3-(4-(benzo[d][1,3]-dioxol-5-yl)phenyl)-1-(pyridin-2-yl)-1H-pyrazol-5-yl tert-butyl carbonate (28)

The title compound was prepared in the same manner as in Example C-1, except that an equimolar amount of benzo[d][1,3]dioxol-5-yl-5-boronic acid (manufactured by Aldrich) was used in place of phenylboronic acid.

Yield: 70%

$^1$H NMR (300 MHz, CDCl$_3$) δ 8.43-8.40 (m, 1H), 8.03-8.00 (m, 1H), 7.92-7.89 (m, 2H), 7.85-7.80 (m, 1H), 7.59-7.56 (m, 2H), 7.21-7.17 (m, 1H), 7.13-7.10 (m, 2H), 6.91-6.88 (m, 1H), 6.54 (s, 1H), 6.01 (s, 2H), 1.57 (s, 9H)

Example C-3

Synthesis of 3-(3'-phenylbiphenyl-4-yl)-1-(pyridin-2-yl)-1H-pyrazol-5-yl tert-butyl carbonate (29)

The title compound was prepared in the same manner as in Example C-1, except that an equimolar amount of 3-biphenylboronic acid (manufactured by Aldrich) was used in place of phenylboronic acid.

Yield: 95%

$^1$H NMR (300 MHz, CDCl$_3$) δ 8.44-8.41 (m, 1H), 8.04-7.95 (m, 3H), 7.86-7.80 (m, 2H), 7.73-7.27 (m, 1H), 7.22-7.17 (m, 1H), 6.57 (s, 1H), 1.58 (s, 9H)

Example C-4

Synthesis of tert-butyl 3-(4-(naphthalene)phenyl)-1-(pyridin-2-yl)-1H-pyrazol-5-yl carbonate (30)

The title compound was prepared in the same manner as in Example C-1, except that an equimolar amount of naphthalen-1-yl-1-boronic acid (manufactured by Aldrich) was used in place of phenylboronic acid.

Yield: 98%

$^1$H NMR (300 MHz, CDCl$_3$) δ 8.44-8.42 (m, 1H), 8.06-7.81 (m, 7H), 7.58-7.42 (m, 6H), 7.22-7.18 (m, 1H), 6.59 (s, 1H)

Example C-5

Synthesis of tert-butyl 3-(3'-(dimethylamino)biphenyl)-1-(pyridin-2-yl)-1H-pyrazol-5-yl carbonate (31)

The title compound was prepared in the same manner as in Example C-1, except that an equimolar amount of 3-(N,N-dimethylamino)phenylboronic acid (manufactured by Aldrich) was used in place of phenylboronic acid.

Yield: 80.5%

$^1$H NMR (300 MHz, CDCl$_3$) δ 8.43-8.41 (m, 1H), 8.04-8.01 (m, 1H), 7.93 (d, 2H, J=8.2 Hz), 7.86-7.80 (m, 1H), 7.66

(d, 2H, J=8.2 Hz), 7.35-7.30 (m, 1H), 7.21-7.17 (m, 1H), 7.00-6.98 (m, 2H), 6.78-6.75 (m, 1H), 6.55 (s, 1H), 3.02 (s, 6H), 1.57 (s, 9H)

Example C-6

Synthesis of 3-(2-(benzo[d][1,3]dioxol-5-yl)phenyl)-1-(pyridin-2-yl)-1H-pyrazol-5-yl tert-butyl carbonate (32)

The title compound was prepared in the same manner as in Example C-1, except that an equimolar amount of each of 3-(2-iodophenyl)-1-(pyridin-2-yl)-1H-pyrazol-5-yl tert-butyl carbonate (22) prepared in Example B-3 and benzo[d][1,3]dioxol-5-yl-5-boronic acid (manufactured by Aldrich) was used in place of Compound 21 prepared in Example B-2 and phenylboronic acid.

Yield: 84%

$^1$H NMR (300 MHz, CDCl$_3$) δ 12.58 (1H, s), 8.26-8.24 (1H, m), 7.98-7.95 (1H, m), 7.90-7.84 (2H, m), 7.42-7.30 (3H, m), 7.16-7.12 (1H, m), 6.78 (3H, s), 5.97 (2H, s), 5.05 (1H, s)

Example C-7

Synthesis of 3-(3'-phenylbiphenyl-2-yl)-1-(pyridin-2-yl)-1H-pyrazol-5-yl tert-butyl carbonate (33)

The title compound was prepared in the same manner as in Example C-6, except that an equimolar amount of 3-biphenylboronic acid (manufactured by Aldrich) was used in place of benzo[d][1,3]dioxol-5-yl-5-boronic acid (manufactured by Aldrich).

Example C-8

Synthesis of 3-(biphenyl-3-yl)-1-(pyridin-2-yl)-1H-pyrazol-5-yl tert-butyl carbonate (34)

The title compound was prepared in the same manner as in Example C-1, except that an equimolar amount of 3-(3-iodophenyl)-1-(pyridin-2-yl)-1H-pyrazol-5-yl tert-butyl carbonate (23) prepared in Example B-4 was used in place of Compound 21 prepared in Example B-2.

Yield: 89%

$^1$H NMR (300 MHz, CDCl$_3$) δ 8.43-8.41 (m, 1H), 8.10 (s, 1H), 8.03 (d, 1H, J=8.3 Hz), 7.86-7.80 (m, 2H), 7.66 (d, 2H, J=7.4 Hz), 7.60-7.57 (m, 1H), 7.52-7.44 (m, 3H), 7.39-7.37 (m, 1H), 7.21-7.17 (m, 1H), 6.57 (s, 1H), 1.57 (s, 9H)

Example C-9

Synthesis of 3-(4'-(benzyloxy)biphenyl-3-yl)-1-(pyridin-2-yl)-1H-pyrazol-5-yl tert-butyl carbonate (35)

The title compound was prepared in the same manner as in Example C-1, except that an equimolar amount of each of 3-(3-iodophenyl)-1-(pyridin-2-yl)-1H-pyrazol-5-yl tert-butyl carbonate (23) prepared in Example B-4 and 4-benzyloxyphenylboronic acid (manufactured by Aldrich) was used in place of Compound 21 prepared in Example B-2 and phenylboronic acid.

Yield: 99%

$^1$H NMR (300 MHz, CDCl$_3$) δ 8.43-8.41 (m, 1H), 8.06-8.01 (m, 2H), 7.85-7.78 (m, 2H), 7.61-7.33 (m, 9H), 7.21-7.17 (m, 1H), 7.07 (d, 2H, J=8.7 Hz), 6.56 (s, 1H), 5.13 (s, 2H), 1.57 (s, 9H)

Example C-10

Synthesis of 3-(4'-bromobiphenyl-3-yl)-1-(pyridin-2-yl)-1H-pyrazol-5-yl tert-butyl carbonate (36)

The title compound was prepared in the same manner as in Example C-9, except that an equimolar amount of 4-bromophenylboronic acid (manufactured by Aldrich) was used in place of 4-benzyloxyphenylboronic acid.

Yield: 66%

$^1$H NMR (300 MHz, CDCl$_3$) δ 8.43-8.42 (m, 1H), 8.06-8.00 (m, 2H), 7.86-7.81 (m, 2H), 7.60-7.49 (m, 6H), 7.22-7.18 (m, 1H), 6.57 (s, 1H), 1.57 (s, 9H)

Example C-11

Synthesis of tert-butyl 3-(3'-formylbiphenyl-3-yl)-1-(pyridin-2-yl)-1H-pyrazol-5-yl carbonate (37)

The title compound was prepared in the same manner as in Example C-9, except that an equimolar amount of 3-formylphenylboronic acid (manufactured by Aldrich) was used in place of 4-benzyloxyphenylboronic acid.

Yield: 48%

$^1$H NMR (300 MHz, CDCl$_3$) δ 10.11 (s, 1H), 8.44-8.42 (m, 1H), 8.16-8.15 (m, 2H), 8.03 (d, 1H, J=8.3 Hz), 7.94-7.81 (m, 4H), 7.65-7.50 (m, 3H), 7.22-7.18 (m, 1H), 6.59 (s, 1H), 1.58 (s, 9H)

Example C-12

Synthesis of tert-butyl 3-(2'-phenoxybiphenyl-3-yl)-1-(pyridin-2-yl)-1H-pyrazol-5-yl carbonate (38)

The title compound was prepared in the same manner as in Example C-9, except that an equimolar amount of 2-phenoxyphenylboronic acid (manufactured by Aldrich) was used in place of 4-benzyloxyphenylboronic acid.

Yield: 56%

$^1$H NMR (300 MHz, CDCl$_3$) δ 8.40-8.39 (m, 1H), 8.03 (s, 1H), 7.95-7.92 (m, 2H), 7.82-7.77 (m, 2H), 7.56-7.52 (m, 2H), 7.42-7.15 (m, 6H), 7.05-6.93 (m, 3H), 6.44 (s, 1H), 1.56 (s, 9H)

Example C-13

Synthesis of 3-(3-(benzo[d][1,3]-dioxol-5-yl)phenyl)-1-(pyridin-2-yl)-1H-pyrazol-5-yl tert-butyl carbonate (39)

The title compound was prepared in the same manner as in Example C-9, except that an equimolar amount of 3,4-(methylenedioxy)phenylboronic acid (manufactured by Aldrich) was used in place of 4-benzyloxyphenylboronic acid.

Yield: 99%

$^1$H NMR (300 MHz, CDCl$_3$) δ 8.43-8.41 (m, 1H), 8.04-8.01 (m, 2H), 7.86-7.78 (m, 2H), 7.52-7.43 (m, 2H), 7.21-7.11 (m, 3H), 6.91-6.89 (m, 1H), 6.56 (s, 1H), 6.01 (s, 2H), 1.57 (s, 9H)

Example C-14

Synthesis of 3-(3'-phenylbiphenyl-3-yl)-1-(pyridin-2-yl)-1H-pyrazol-5-yl tert-butyl carbonate (40)

The title compound was prepared in the same manner as in Example C-9, except that an equimolar amount of 3-phenylboronic acid (manufactured by Aldrich) was used in place of 4-benzyloxyphenylboronic acid.

Yield: 90%

¹H NMR (300 MHz, CDCl₃) δ 8.43-8.41 (m, 1H), 8.15 (s, 1H), 8.04 (d, 1H, J=8.3 Hz), 7.88-7.80 (m, 3H), 7.69-7.45 (m, 9H), 7.40-7.35 (m, 1H), 7.22-7.17 (m, 1H), 6.59 (s, 1H), 1.58 (s, 9H)

Example C-15

Synthesis of tert-butyl 3-(3-(naphthalen-1-yl)phenyl)-1-(pyridin-2-yl)-1H-pyrazol-5-yl carbonate (41)

The title compound was prepared in the same manner as in Example C-9, except that an equimolar amount of 1-naphthaleneboronic acid (manufactured by Aldrich) was used in place of 4-benzyloxyphenylboronic acid.

Yield: 84%

¹H NMR (300 MHz, CDCl₃) δ 8.41-8.39 (m, 1H), 8.01-7.87 (m, 6H), 7.82-7.76 (m, 1H), 7.57-7.41 (m, 6H), 7.19-7.15 (m, 1H), 6.55 (s, 1H), 1.56 (s, 9H)

Example C-16

Synthesis of tert-butyl 3-(3'-(dimethylamino)biphenyl-3-yl)-1-(pyridin-2-yl)-1H-pyrazol-5-yl carbonate (42)

The title compound was prepared in the same manner as in Example C-9, except that an equimolar amount of 3-(N,N-dimethylamino)phenylboronic acid (manufactured by Aldrich) was used in place of 4-benzyloxyphenylboronic acid.

Yield: 90%

¹H NMR (300 MHz, CDCl₃) δ 8.42-8.40 (m, 1H), 8.07-8.01 (m, 2H), 7.86-7.79 (m, 2H), 7.59-7.56 (m, 1H), 7.50-7.45 (m, 1H), 7.36-7.30 (m, 1H), 7.20-7.16 (m, 1H), 7.01-6.97 (m, 2H), 6.78-6.75 (m, 1H), 6.56 (s, 1H), 3.02 (s, 6H), 1.57 (s, 9H)

Example C-17

Synthesis of tert-butyl 3-(4'-methoxybiphenyl-4-yl)-1-(pyridin-2-yl)-1H-pyrazol-5-yl carbonate (43)

The title compound was prepared in the same manner as in Example C-1, except that an equimolar amount of each of 3-(4-iodophenyl)-1-(pyridin-2-yl)-1H-pyrazol-5-yl tert-butyl carbonate (24) prepared in Example B-5 and 4-methoxyphenylboronic acid (manufactured by Aldrich) was used in place of Compound 21 prepared in Example B-2 and phenylboronic acid.

Yield: 98%

¹H NMR (300 MHz, CDCl₃) δ 8.43-8.41 (m, 1H), 8.04-8.01 (m, 1H), 7.92 (d, 2H, J=8.2 Hz), 7.86-7.80 (m, 1H), 7.63-7.57 (m, 4H), 7.21-7.17 (m, 1H), 7.00 (d, 2H, J=8.7 Hz), 6.55 (s, 1H), 3.86 (s, 3H), 1.59 (s, 9H)

Example C-18

Synthesis of 3-(4'-(benzyloxy)biphenyl-4-yl)-1-(pyridin-2-yl)-1H-pyrazol-5-yl tert-butyl carbonate (44)

The title compound was prepared in the same manner as in Example C-17, except that an equimolar amount of 4-benzyloxyphenylboronic acid (manufactured by Aldrich) was used in place of 4-methoxyphenylboronic acid.

Yield: 98%

¹H NMR (300 MHz, CDCl₃) δ 8.43-8.41 (m, 1H), 8.03-8.01 (m, 1H), 7.92 (d, 2H, J=8.3 Hz), 7.86-7.80 (m, 1H), 7.63-7.56 (m, 4H), 7.48-7.33 (m, 5H), 7.21-7.17 (m, 1H), 7.09-7.05 (m, 2H), 6.54 (s, 1H), 1.57 (s, 9H)

Example C-19

Synthesis of 3-(4'-bromobiphenyl-4-yl)-1-(pyridin-2-yl)-1H-pyrazol-5-yl tert-butyl carbonate (45)

The title compound was prepared in the same manner as in Example C-17, except that an equimolar amount of 4-bromophenylboronic acid (manufactured by Aldrich) was used in place of 4-methoxyphenylboronic acid.

Yield: 71%

¹H NMR (300 MHz, CDCl₃) δ 8.43-8.41 (m, 1H), 8.03-8.00 (m, 1H), 7.95 (d, 2H, J=8.2 Hz), 7.86-7.81 (m, 1H), 7.63-7.49 (m, 6H), 7.22-7.18 (m, 1H), 6.56 (s, 1H), 1.58 (s, 9H)

Example C-20

Synthesis of 3-(3'-formylbiphenyl-4-yl)-1-(pyridin-2-yl)-1H-pyrazol-5-yl tert-butyl carbonate (46)

The title compound was prepared in the same manner as in Example C-17, except that an equimolar amount of 3-formylphenylboronic acid (manufactured by Aldrich) was used in place of 4-methoxyphenylboronic acid.

Yield: 58%

¹H NMR (300 MHz, CDCl₃) δ 10.09 (s, 1H), 8.44-8.42 (m, 1H), 8.14 (s, 1H), 8.02-7.83 (m, 6H), 7.70-7.61 (m, 3H), 7.22-7.18 (m, 1H), 6.58 (s, 1H), 1.58 (s, 9H)

Example C-21

Synthesis of tert-butyl 3-(2'-phenoxybiphenyl-4-yl)-1-(pyridin-2-yl)-1H-pyrazol-5-yl carbonate (47)

The title compound was prepared in the same manner as in Example C-17, except that an equimolar amount of 2-phenoxyphenylboronic acid (manufactured by Aldrich) was used in place of 4-methoxyphenylboronic acid.

Yield: 63%

¹H NMR (300 MHz, CDCl₃) δ 8.41-8.39 (m, 1H), 8.00 (d, 1H, J=8.28 Hz), 7.87-7.78 (m, 3H), 7.62 (d, 2H, J=8.1 Hz), 7.52-7.49 (m, 1H), 7.34-7.15 (m, 5H), 7.04-6.91 (m, 4H), 6.51 (s, 1H), 1.56 (s, 9H)

Example C-22

Synthesis of 3-(biphenyl-4-yl)-1-(pyrimidin-2-yl)-1H-pyrazol-5-yl tert-butyl carbonate (48)

The title compound was prepared in the same manner as in Example C-1, except that an equimolar amount of each of 3-(4-iodophenyl)-1-(pyrimidin-2-yl)-1H-pyrazol-5-yl tert-butyl carbonate (25) prepared in Example B-6 and phenylboronic acid (manufactured by Aldrich) was used in place of Compound 21 prepared in Example B-2 and phenylboronic acid.

Yield: 95%

¹H NMR (300 MHz, CDCl₃) δ: 8.44-8.41 (1H, m), 8.04-7.95 (3H, m), 7.86-7.80 (2H, m), 7.73-7.27 (11H, m), 7.22-7.17 (1H, m), 6.57 (1H, s), 1.58 (9H, s).

Example C-23

Synthesis of 3-(4-(benzo[d][1,3]dioxol-5-1 phenyl)-1-(pyrimidin-2-yl)-1H-pyrazol-5-yl tert-butyl carbonate (49)

The title compound was prepared in the same manner as in Example C-22, except that an equimolar amount of 3,4-(methylenedioxy)phenylboronic acid (manufactured by Aldrich) was used in place of phenylboronic acid.
Yield: 74%
$^1$H NMR (300 MHz, CDCl$_3$) δ 8.80 (d, 2H, J=4.8 Hz), 7.98 (d, 2H, J=8.5 Hz), 7.58 (d, 2H, J=8.6 Hz), 7.24-7.21 (m, 1H), 7.14-7.10 (m, 2H), 6.89 (d, 1H, J=8.5 Hz), 6.60 (s, 1H), 6.00 (s, 2H), 1.59 (s, 9H)

Example C-24

Synthesis of 3-(3'-phenylbiphenyl-4-yl)-1-(pyrimidin-2-yl)-1H-pyrazol-5-yl tert-butyl carbonate (50)

The title compound was prepared in the same manner as in Example C-22, except that an equimolar amount of 3-biphenylboronic acid (manufactured by Aldrich) was used in place of phenylboronic acid.
Yield: 90%
$^1$H NMR (300 MHz, CDCl$_3$) δ 8.80 (d, 2H, J=4.8 Hz), 8.03 (d, 2H, J=8.5 Hz), 7.85-7.84 (m, 1H), 7.73-7.44 (m, 9H), 7.40-7.35 (m, 1H), 7.25-7.21 (m, 1H), 6.62 (s, 1H), 1.59 (s, 9H)

Example C-25

Synthesis of 2-(3-(4'-bromobiphenyl-4-yl)-5-(triisopropylsilyloxy)-1H-pyrazol-1-yl)pyridine (51)

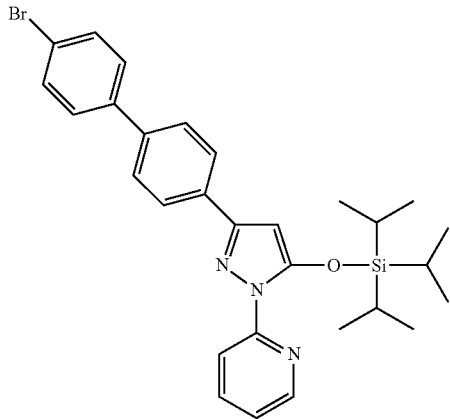 [SMILES: CC(C)[Si](Oc1cc(-c2ccc(-c3ccc(Br)cc3)cc2)nn1-c1ccccn1)(C(C)C)C(C)C]

3-(4-iodophenyl)-1-(pyridin-2-yl)-1H-pyrazol-5-ol (1 equivalent) was dissolved in CH$_2$Cl$_2$ (5 mL) to which 3 equivalents of triethylamine were then added. Under stream of nitrogen, 2 equivalents of triisopropylsilyl chloride (TIP-SCl) were added thereto at 0° C., followed by stirring at room temperature. After 10 minutes, the solution was concentrated by distillation under reduced pressure and hexane was added thereto, followed by washing with a saturated NaHCO$_3$ aqueous solution.
After extraction with hexane twice, the organic layer was dried over anhydrous MgSO$_4$, filtered, concentrated and then dried under vacuum to afford 2-(3-(4-iodophenyl)-5-(triisopropylsilyloxy)-1H-pyrazol-1-yl)pyridine. 1 mmol of the thus-prepared compound was charged in a 50 mL round-bottom flask and dissolved in 1,4-dioxane (10 mL), and 4-bromophenylboronic acid (2.5 equivalents, manufactured by Aldrich) and K$_3$PO$_4$ (3 equivalents) were added thereto. Thereafter, PdCl$_2$(dppf) (0.08 equivalents, manufactured by Aldrich) and dppf (1,1'-bis(diphenylphosphino)ferrocene, 0.04 equivalents, manufactured by Aldrich) were added thereto, followed by heating at 100° C. for 10 minutes. After the solid was filtered through Celite, the organic layer was concentrated under reduced pressure, dissolved in ethyl acetate and then washed with water. The organic layer was dried over anhydrous MgSO$_4$ and concentrated. The resulting residue was purified by column chromatography (n-hexane:EA=8:1) to afford the title compound.
$^1$H NMR (300 MHz, CDCl$_3$) 8.69-8.59 (m, 1H), 7.97-9.93 (m, 2H), 7.81-7.72 (m, 2H), 7.61-7.48 (m, 6H), 7.26-7.22 (m, 1H), 6.00 (s, 1H), 1.37-1.26 (m, 3H), 1.12-1.09 (m, 18H)

Example C-26

Synthesis of 2-(3-(biphenyl-4-yl)-5-(diphenylboryloxy)-1H-pyrazol-1-yl)pyridine (52)

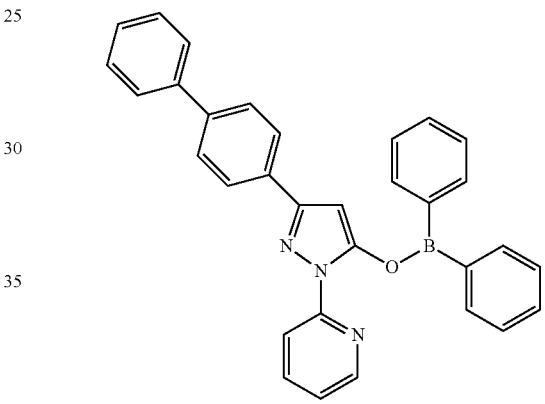

1 mmol of 3-(4-iodophenyl)-1-(pyridin-2-yl)-1H-pyrazol-5-ol was charged in a 50 mL round-bottom flask and dissolved in 1,4-dioxane (10 mL), and phenylboronic acid (2.5 equivalents, manufactured by Aldrich) and K$_3$PO$_4$ (3 equivalents) were added thereto. Thereafter, PdCl$_2$(dppf) (0.08 equivalents, manufactured by Aldrich) and dppf (1,1'-bis (diphenylphosphino)ferrocene, 0.04 equivalents, manufactured by Aldrich) were added thereto, followed by heating at 100° C. for 10 minutes. After the solid was filtered through Celite, the organic layer was concentrated under reduced pressure, dissolved in ethyl acetate and then washed with water. The organic layer was dried over anhydrous MgSO$_4$ and concentrated. The resulting residue was purified by column chromatography (n-hexane:EA=8:1 (v/v)) to afford the title compound.
$^1$H NMR (300 MHz, CDCl$_3$) δ 8.16-8.09 (m, 2H), 7.94-7.88 (m, 3H), 7.55-7.61 (m, 4H), 7.40-7.29 (m, 3H), 7.29-7.20 (m, 11H), 6.00 (s, 1H)

D. Synthesis of Compound of Formula I-4

Example D-1

Synthesis of 3-(biphenyl-4-yl)-1-(pyridin-2-yl)-1H-pyrazol-5-ol (54)

0.5 mmol of Compound 27 prepared in Example C-1 was charged in a 25 mL round-bottom flask and dissolved in methylene chloride (5 mL) to make a solution to which trifluoroacetic acid (TFA, 5 equivalents) was then added, followed by stirring at room temperature for 30 minutes. After completion of the reaction was confirmed by TLC, the reaction liquid was washed three times with distilled water, and the organic layer was dried over anhydrous $MgSO_4$ and concentrated to afford the title compound.

Yield: 93.4%

$^1$H NMR (300 MHz, $CDCl_3$) δ 8.31-8.28 (m, 1H), 8.10-8.07 (m, 1H), 7.96-7.89 (m, 3H), 7.69-7.63 (m, 4H), 7.49-7.44 (m, 2H), 7.39-7.33 (m, 1H), 7.20-7.16 (m, 1H), 5.99 (s, 1H)

Example D-2

Synthesis of 3-(4-(benzo[d][1,3]-dioxol-5-yl)phenyl)-1-(pyridin-2-yl)-1H-pyrazol-5-ol (55)

The title compound was prepared in the same manner as in Example D-1, except that an equimolar amount of Compound 28 of Example C-2 was used in place of Compound 27 of Example C-1.

Yield: 70%

$^1$H NMR (300 MHz, $CDCl_3$) δ 8.29-8.27 (m, 1H), 8.08-8.05 (m, 1H), 7.93-7.87 (m, 3H), 7.59-7.55 (m, 2H), 7.19-7.14 (m, 1H), 7.12-7.09 (m, 2H), 6.90-6.88 (m, 1H), 6.00 (s, 2H), 5.96 (s, 1H)

Example D-3

Synthesis of 3-(3'-phenylbiphenyl-4-yl)-1-(pyridin-2-yl)-1H-pyrazol-5-ol (56)

The title compound was prepared in the same manner as in Example D-1, except that an equimolar amount of Compound 29 of Example C-3 was used in place of Compound 27 of Example C-1.

Yield: 58%

$^1$H NMR (300 MHz, $CDCl_3$) δ 12.84-12.83 (bs, 1H) 8.30-8.28 (m, 1H), 8.09-8.06 (m, 1H), 7.97-7.85 (m, 4H), 7.73-7.45 (m, 9H), 7.40-7.36 (m, 1H), 7.20-7.16 (m, 1H), 6.00 (s, 1H)

Example D-4

Synthesis of 3-(4-(naphthalen-1-yl)phenyl)-1-(pyridin-2-yl)-1H-pyrazol-5-ol (57)

The title compound was prepared in the same manner as in Example D-1, except that an equimolar amount of Compound 30 of Example C-4 was used in place of Compound 27 of Example C-1.

Yield: 71%

$^1$H NMR (300 MHz, $CDCl_3$) δ 12.89 (bs, 1H), 8.31-8.29 (m, 1H), 8.10-8.08 (m, 1H), 8.00-7.86 (m, 6H), 7.58-7.41 (m, 6H), 7.21-7.17 (m, 1H), 6.03 (s, 1H)

Example D-5

Synthesis of 3-(3'-(dimethylamino)biphenyl-4-yl)-(pyridin-2-yl)-1H-pyrazol-5-ol (58)

The title compound was prepared in the same manner as in Example D-1, except that an equimolar amount of Compound 31 of Example C-5 was used in place of Compound 27 of Example C-1.

Yield: 99%

$^1$H NMR (300 MHz, $CDCl_3$) δ 10.26 (bs, 1H), 8.31-8.30 (m, 1H), 8.10-8.07 (m, 1H), 7.98-7.90 (m, 3H), 7.75-7.50 (m, 5H), 7.50-7.49 (m, 1H), 7.22-7.18 (m, 1H), 5.99 (s, 1H), 3.27 (s, 6H)

Example D-6

Synthesis of 3-(2-(benzo[d][1,3]dioxol-5-yl)phenyl)-1-(pyridin-2-yl)-1H-pyrazol-5-ol (59)

The title compound was prepared in the same manner as in Example D-1, except that an equimolar amount of Compound 32 of Example C-6 was used in place of Compound 27 of Example C-1.

Yield: 84%

$^1$H NMR (300 MHz, $CDCl_3$) δ 12.58 (bs, 1H), 8.26-8.24 (m, 1H), 7.98-7.95 (m, 1H), 7.90-7.84 (m, 2H), 7.42-7.30 (m, 3H), 7.16-7.12 (m, 1H), 6.78 (s, 3H), 5.97 (s, 2H), 5.05 (s, 1H)

Example D-7

Synthesis of 3-(3'-phenylbiphenyl-2-yl)-1-(pyridin-2-yl)-1H-pyrazol-5-ol (60)

The title compound was prepared in the same manner as in Example D-1, except that an equimolar amount of Compound 33 of Example C-7 was used in place of Compound 27 of Example C-1.

Yield: 82%

$^1$H NMR (300 MHz, $CDCl_3$) δ 8.10-8.06 (m, 2H), 7.67 (s, 1H), 7.56-7.47 (m, 5H), 7.40-7.26 (m, 9H), 6.04 (s, 1H)

Example D-8

Synthesis of 3-biphenyl-3-yl)-1-(pyridin-2-yl)-1H-pyrazol-5-ol (61)

The title compound was prepared in the same manner as in Example D-1, except that an equimolar amount of Compound 34 of Example C-8 was used in place of Compound 27 of Example C-1.

Yield: 90%

$^1$H NMR (300 MHz, $CDCl_3$) δ 8.30-8.27 (m, 1H), 8.10-8.06 (m, 2H), 7.93-7.87 (m, 1H), 7.84-7.82 (m, 1H), 7.69-7.66 (m, 2H), 7.60-7.57 (m, 1H), 7.52-7.44 (m, 3H), 7.40-7.34 (m, 1H), 7.19-7.15 (m, 1H), 6.00 (s, 1H)

Example D-9

Synthesis of 3-(4'-(benzyloxy)biphenyl-3-yl)-1-(pyridin-2-yl)-1H-pyrazol-5-ol (62)

The title compound was prepared in the same manner as in Example D-1, except that an equimolar amount of Compound 35 of Example C-9 was used in place of Compound 27 of Example C-1.

Yield: 89%

$^1$H NMR (300 MHz, $CDCl_3$) δ 8.28-8.26 (m, 1H), 8.08-8.05 (m, 2H), 7.92-7.86 (m, 1H), 7.79-7.77 (m, 1H), 7.61-7.31 (m, 9H), 7.18-7.05 (m, 3H), 5.98 (s, 1H), 5.12 (s, 2H)

Example D-10

Synthesis of 3-(4'-bromobiphenyl-3-yl)-1-(pyridin-2-yl)-1H-pyrazol-5-ol (63)

The title compound was prepared in the same manner as in Example D-1, except that an equimolar amount of Compound 36 of Example C-10 was used in place of Compound 27 of Example C-1.

Yield: 84%

$^1$H NMR (300 MHz, CDCl$_3$) δ 12.85-12.83 (bs, 1H), 8.30-8.28 (m, 1H), 8.08-8.06 (m, 2H), 7.94-7.88 (m, 1H), 7.84-7.81 (m, 1H), 7.60-7.46 (m, 6H), 7.20-7.16 (m, 1H), 5.99 (s, 1H)

Example D-11

Synthesis of 3-(3'-formylbiphenyl-3-yl)-1-(pyridin-2-yl)-1H-pyrazol-5-ol (64)

The title compound was prepared in the same manner as in Example D-1, except that an equimolar amount of Compound 37 of Example C-11 was used in place of Compound 27 of Example C-1.

Example D-12

Synthesis of 3-(2'-phenoxybiphenyl-3-yl)-1-(pyridin-2-yl)-1H-pyrazol-5-ol (65)

The title compound was prepared in the same manner as in Example D-1, except that an equimolar amount of Compound 38 of Example C-12 was used in place of Compound 27 of Example C-1.

Yield: 80%

$^1$H NMR (300 MHz, CDCl$_3$) δ 12.76 (bs, 1H), 8.27-8.25 (m, 1H), 8.03-7.77 (m, 4), 7.55-6.93 (m, 12H), 5.86 (s, 1H)

Example D-13

Synthesis of 3-(3-(benzo[d][1,3]dioxol-5-yl)phenyl)-1-(pyridin-2-yl)-1H-pyrazol-5-ol (66)

The title compound was prepared in the same manner as in Example D-1, except that an equimolar amount of Compound 39 of Example C-13 was used in place of Compound 27 of Example C-1.

Yield: 98%

$^1$H NMR (300 MHz, CDCl$_3$) δ 8.30-8.28 (m, 1H), 8.09 (d, 1H, J=8.4 Hz), 8.03-8.02 (m, 1H), 7.94-7.88 (m, 1H), 7.80-7.76 (m, 1H), 7.52-7.46 (m, 2H), 7.20-7.12 (m, 3H), 6.92-6.89 (m, 1H), 6.02 (s, 2H), 5.99 (s, 1H)

Example D-14

Synthesis of 3-(3'-phenylbiphenyl-3-yl)-1-(pyridin-2-yl)-1H-pyrazol-5-ol (67)

The title compound was prepared in the same manner as in Example D-1, except that an equimolar amount of Compound 40 of Example C-14 was used in place of Compound 27 of Example C-1.

Yield: 85%

$^1$H NMR (300 MHz, CDCl$_3$) δ 8.31-8.28 (m, 1H), 8.6-8.15 (m, 1H), 8.10 (d, 1H, J=8.4 Hz), 7.94-7.84 (m, 3H), 7.70-7.45 (m, 9H), 7.41-7.36 (m, 1H), 7.20-7.16 (m, 1H), 6.02 (s, 1H)

Example D-15

Synthesis of 3-(3-(naphthalen-1-yl)phenyl)-1-(pyridin-2-yl)-1H-pyrazol-5-ol (68)

The title compound was prepared in the same manner as in Example D-1, except that an equimolar amount of Compound 41 of Example C-15 was used in place of Compound 27 of Example C-1.

Yield: 97%

$^1$H NMR (300 MHz, CDCl$_3$) δ 12.81 (bs, 1H), 8.27-8.25 (m, 1H), 8.03-8.00 (m, 2H), 7.95-7.83 (m, 5H), 7.57-7.40 (m, 6H), 7.17-7.12 (m, 1H), 5.97 (s, 1H)

Example D-16

Synthesis of 3-(3'-(dimethylamino)biphenyl-3-yl)-1-(pyridin-2-yl)-1H-pyrazol-5-ol (69)

The title compound was prepared in the same manner as in Example D-1, except that an equimolar amount of Compound 42 of Example C-16 was used in place of Compound 27 of Example C-1.

Yield: 99%

$^1$H NMR (300 MHz, CDCl$_3$) δ 13.09 (bs, 1H), 8.31-8.29 (m, 1H), 8.10-8.07 (m, 2H), 7.95-7.84 (m, 2H), 7.69-7.44 (m, 6H), 7.22-7.17 (m, 1H), 6.00 (s, 1H), 3.23 (s, 6H)

Example D-17

Synthesis of 3-(4'-methoxybiphenyl-4-yl)-1-(pyridin-2-yl)-1H-pyrazol-5-ol] (70)

The title compound was prepared in the same manner as in Example D-1, except that an equimolar amount of Compound 43 of Example C-17 was used in place of Compound 27 of Example C-1.

Yield: 62%

$^1$H NMR (300 MHz, CDCl$_3$) δ 8.30-8.28 (m, 1H), 8.08-8.05 (m, 1H), 7.94-7.88 (m, 3H), 7.63-7.55 (m, 4H), 7.19-7.15 (m, 1H), 7.00 (d, 2H, J=8.8 Hz), 5.97 (s, 1H), 3.86 (s, 3H)

Example D-18

Synthesis of 3-(4'-(benzyloxy)biphenyl-4-yl)-1-(pyridin-2-yl)-1H-pyrazol-5-ol (71)

The title compound was prepared in the same manner as in Example D-1, except that an equimolar amount of Compound 44 of Example C-18 was used in place of Compound 27 of Example C-1.

Yield: 85%

$^1$H NMR (300 MHz, CDCl$_3$) δ 12.85-12.83 (bs, 1H), 8.30-8.28 (m, 1H), 8.08-8.05 (m, 1H), 7.93-7.89 (m, 3H), 7.63-7.56 (m, 4H), 7.50-7.29 (m, 5H), 7.19-7.15 (m, 1H), 7.08-7.05 (m, 2H), 5.97 (s, 1H), 5.12 (s, 1H)

Example D-19

Synthesis of 3-(4'-bromobiphenyl-4-yl)-1-(pyridin-2-yl)-1H-pyrazol-5-ol (72)

The title compound was prepared in the same manner as in Example D-1, except that an equimolar amount of Compound 45 of Example C-19 was used in place of Compound 27 of Example C-1.

Yield: 87%

$^1$H NMR (300 MHz, CDCl$_3$) δ 12.87-12.80 (bs, 1H), 8.29-8.27 (m, 1H), 8.07-8.04 (m, 1H), 7.94-7.87 (m, 3H), 7.62-7.48 (m, 6H), 7.20-7.15 (m, 1H), 5.97 (s, 1H)

Example D-20

Synthesis of 3-(3'-formylbiphenyl-4-yl)-1-(pyridin-2-yl)-1H-pyrazol-5-ol (73)

The title compound was prepared in the same manner as in Example D-1, except that an equimolar amount of Compound 46 of Example C-20 was used in place of Compound 27 of Example C-1.

Example D-21

Synthesis of 3-(2'-phenoxybiphenyl-4-yl)-1-(pyridin-2-yl)-1H-pyrazol-5-ol (74)

The title compound was prepared in the same manner as in Example D-1, except that an equimolar amount of Compound 47 of Example C-21 was used in place of Compound 27 of Example C-1.
Yield: 86%
$^1$H NMR (300 MHz, CDCl$_3$) δ 12.78 (bs, 1H), 8.26-8.25 (m, 1H), 8.04-7.83 (m, 4H), 7.62-7.48 (m, 3H), 7.33-6.92 (m, 9H), 5.93 (m, 1H)

Example D-22

Synthesis of 3-(biphenyl-4-yl)-1-(pyrimidin-2-yl)-1H-pyrazol-5-ol (75)

The title compound was prepared in the same manner as in Example D-1, except that an equimolar amount of Compound 48 of Example C-22 was used in place of Compound 27 of Example C-1.
Yield: 92%
$^1$H NMR (300 MHz, CDCl$_3$) δ 8.79 (d, 2H, J=4.9 Hz), 8.01 (d, 2H, J=8.4 Hz), 7.67-7.63 (m, 4H), 7.47-7.42 (m, 2H), 7.38-7.32 (m, 1H), 7.25-7.21 (m, 1H), 6.05 (s, 1H)

Example D-23

Synthesis of 3-(4-(benzo[d][1,3]-dioxol-5-yl)phenyl)-1-(pyrimidin-2-yl)-1H-pyrazol-5-ol (76)

The title compound was prepared in the same manner as in Example D-1, except that an equimolar amount of Compound 49 of Example C-23 was used in place of Compound 27 of Example C-1.
Yield: 78%
$^1$H NMR (300 MHz, CDCl$_3$) δ 8.79 (d, 2H, J=4.9 Hz), 7.98 (d, 2H, J=8.2 Hz), 7.58 (d, 2H, J=8.2 Hz), 7.26-7.22 (m, 1H), 7.13-7.11 (m, 2H), 6.89 (d, 1H, J=8.5 Hz), 6.04 (s, 1H), 6.00 (s, 2H)

Example D-24

Synthesis of 3-(3'-phenylbiphenyl-4-yl)-1-(pyrimidin-2-yl)-1H-pyrazol-5-ol (77)

The title compound was prepared in the same manner as in Example D-1, except that an equimolar amount of Compound 50 of Example C-24 was used in place of Compound 27 of Example C-1.
Yield: 93%
$^1$H NMR (300 MHz, CDCl$_3$) δ 8.78 (d, 2H, J=4.9 Hz), 8.01 (d, 2H, J=8.3 Hz), 7.85-7.83 (m, 1H), 7.73-7.44 (m, 9H), 7.39-7.34 (m, 1H), 7.23-7.22 (m, 1H), 6.06 (s, 1H)

Example E-1

Synthesis of 3-phenyl-4-propyl-1-(pyridin-2-yl)-1H-pyrazol-5-ol (78)

Ethyl 2-benzoylpentanoate (355 mg, 1.5 mmol) was dissolved in 5 mL of ethanol to which 2-hydrazinopyridine (163 mg, 1.5 mmol) was then added, followed by refluxing at 100° C. After 20 hours, ethanol was concentrated, followed by extraction with ethyl acetate. The extract was washed two or three times with water, and the organic layer was dried over anhydrous MgSO$_4$ and then concentrated. The resulting residue was purified by column chromatography (n-hexane:EA=10:1) to afford the title compound.
Yield: 80%
$^1$H NMR (300 MHz, CDCl$_3$) δ 12.50 (bs, 1H), 8.27-8.24 (m, 1H), 8.00 (d, 1H, J=8.4 Hz), 7.87-7.81 (m, 1H), 7.72-7.69 (m, 1H), 7.46-7.36 (m, 3H), 7.14-7.10 (m, 1H), 2.54 (t, 2H, J=7.5 Hz), 1.60 (q, 2H, J=7.5 Hz), 0.94 (t, 3H, J=7.3 Hz)

Example E-2

Synthesis of 4-benzyl-3-phenyl-1-(pyridin-2-yl)-1H-pyrazol-5-ol (79)

Ethyl 2-benzyl-3-oxo-3-phenylpropentanoate (530 mg, 1.87 mmol) was dissolved in 5 mL of ethanol to which 2-hydrazinopyridine (204 mg, 1.8 mmol) was then added, followed by refluxing at 100° C. After 20 hours, ethanol was concentrated, followed by extraction with ethyl acetate. The extract was washed two or three times with water, and the organic layer was dried over anhydrous MgSO$_4$ and then concentrated. The resulting residue was purified by column chromatography (n-hexane:EA=10:1 (v/v)) to afford the title compound.
Yield: 92%
$^1$H NMR (300 MHz, CDCl$_3$) δ 12.66 (bs, 1H), 8.27-8.25 (m, 1H), 8.03 (d, 1H, J=8.4 Hz), 7.89-7.84 (m, 1H), 7.64-7.62 (m, 2H), 7.40-7.33 (m, 3H), 7.27-7.24 (m, 4H), 7.19-7.12 (m, 2H), 3.93 (s, 2H)

Experimental Example 1

Inhibitory Effects of Inventive Compounds on Generation of Reactive Oxygen Species A kidney was isolated from a rat (*Rattus norvegicus*) and washed with phosphate buffered saline (PBS). The tissue was soaked in 20 mL of PBS buffer containing a protease inhibitor (Aprotinin 1 μg/mL-USB 11388, Leupeptin 1 μg/mL-USB-18413), finely disrupted using a mixer, and then transferred to a 50 mL conical tube (SPL 50050), followed by centrifugation at 10000 g for 10 minutes (MF-600 plus, Hanil) to sediment the undisrupted tissue. The supernatant was separated and collected in a fresh tube. The tube was placed in ice and subjected to sonication about 4 times each cycle for 30 seconds until the supernatant became clear (Branson Digital Sonifier, Model CE Converter 102C). The supernatant was transferred to a high-speed centrifugation tube (Beckman 331372) and then centrifuged at 100000 g for 1 hour (Optima™ L-90 K Preparative Ultracentrifuge, SW41Ti rotor, Beckman). After the supernatant was discarded, the remaining pellet was washed once with cold PBS and dissolved in 500 μL of cold PBS containing a protease inhibitor to obtain a murine kidney membrane.

Reactive oxygen species generated in the thus-obtained kidney membrane was analyzed by a lucigenin-based assay.

[Since lucigenin, when it is in a normal state (reduced form), does not generate luminescence, but when it is converted into an oxidized form by the action of reactive oxygen species, generates luminescence, the amount of reactive oxygen species is measured by analyzing the intensity of the generated luminescence using a luminometer].

Specifically, each of the compounds synthesized in Examples of the present invention (40 µM, 10 µM, 2.5 µM, 0.625 µM, and 0 µM) was placed in a luminescence assay microplate, and the isolated kidney membrane and lucigenin were sequentially added thereto, followed by incubation at 37° C. for 10 minutes. Then, the intensity of luminescence was measured in a luminometer (MicroLumatPlus LB96V Microplate Luminometer, Berthold) to assay the generation of reactive oxygen species in the murine kidney membrane, followed by calculating an $EC_{50}$ value of the inventive compounds.

TABLE 1

| Compound No. | $EC_{50}$ (µM) |
| --- | --- |
| 15 | 1.2 |
| 16 | 2.5 |
| 17 | 0.7 |
| 18 | 0.45 |
| 19 | 0.8 |
| 20 | 1.5 |
| 26 | 1.3 |
| 48 | 1.2 |
| 51 | 0.4 |
| 52 | 0.5 |
| 54 | 0.4 |
| 55 | 0.5 |
| 59 | 1.4 |
| 61 | 0.4 |
| 65 | 0.625 |
| 67 | 0.4 |
| 72 | 2.5 |
| 74 | 0.4 |
| 75 | 0.6 |
| 78 | 10 |
| 79 | 3 |

As shown in Table 1, the compounds of the present invention were capable of inhibiting the generation of reactive oxygen species even at a low dose. Therefore, it can be seen from the above experiment that the compounds of the present invention have an excellent inhibitory effect on the generation of reactive oxygen species.

Experimental Example 2

Inhibitory Effects of Inventive Compounds on Osteoclast Differentiation

Bone marrow cells were collected from 4 to 5-week old male mice (C57BL/6J).

Specifically, mice were sacrificed by cervical dislocation, and femur and tibia were extracted while removing muscles adhered around the bone with scissors and soaked in phosphate buffered saline (PBS). A 1 mL syringe filled with α-minimal essential medium (α-MEM) was put into one end of the femur and tibia from which bone marrow cells were then harvested.

The bone marrow cells were cultured to obtain macrophages. Specifically, the above-obtained bone marrow cells were placed in a 50 mL tube and centrifuged at 1500 rpm for 5 minutes. The supernatant was discarded, and a 3:1 mixture of a Gey's solution and PBS was added, followed by maintenance at room temperature for about 2 to 3 minutes. After another centrifugation (1500 rpm, 5 minutes), the supernatant was discarded, α-MEM was added, followed by stirring, and then the cells were cultured in a 10 cm cell culture dish at 37° C. for 24 hours. After performing the $3^{rd}$ centrifugation (1500 rpm, 5 minutes), the supernatant was discarded, a culture medium and a macrophage differentiation factor, rhM-CSF (30 ng/mL) were added, and then the cells were cultured in a 10 cm cell culture dish at 37° C. for 3 days. After 3 days, macrophages adhered to the dish were scraped and collected in a tube, followed by centrifugation (1500 rpm, 5 minutes).

The macrophages were cultured to induce cellular differentiation thereof into osteoclasts. Specifically, the above-obtained macrophages were aliquoted at a density of $2 \times 10^4$ cells/well in a 48-well cell culture dish, followed by culture for 24 hours. rhM-CSF (30 ng/mL) and an osteoclast differentiation factor, RANKL (200 ng/mL) were added to the culture medium, followed by culture to induce cellular differentiation thereof into osteoclasts. At this time, as for an experimental group, each of the compounds synthesized in Examples of the present invention (compounds synthesized in Examples A-18, A-19, C-22, D-6, D-22, D-23 and D-24) at a varying concentration of 3 µM, 1 µM, 0.33 µM and 0.1 µM was added to the culture medium, and as for a control group, DMSO was added at a varying concentration of 3 µM, 1 µM, 0.33 µM and 0.1 µM.

After 24 hours, the culture medium in the 48-well cell culture dish was removed and replaced with a fresh medium, followed by cell culture at 37° C. while exchanging the culture medium every two days.

After further culturing for 5 days from the day on which each of the compounds synthesized in Examples of the present invention was added to the medium, the medium to which each of the compounds synthesized in Examples of the present invention was added and the control group medium were respectively fixed in a 3.7% formalin solution, subjected to tartrate resistant acid phosphatase (TRAP) staining, and examined under a light microscope. Specifically, the TRAP staining was carried out as follows: The cells were fixed in 3.7% formaldehyde at room temperature for 15 minutes, and washed twice with distilled water. A staining solution, which was prepared by mixing acetate, Fast Gargnet GBC base, naphthol AS-BI phosphate, sodium nitride and tartrate in the ratio described in the instructions attached to an Acid Phosphatase, Leukocyte (TRAP) Kit™ (Sigma Co.), was added at a dose of 200 µL/well, followed by reacting with the cells at 37° C. for 20 minutes.

Figure 2:
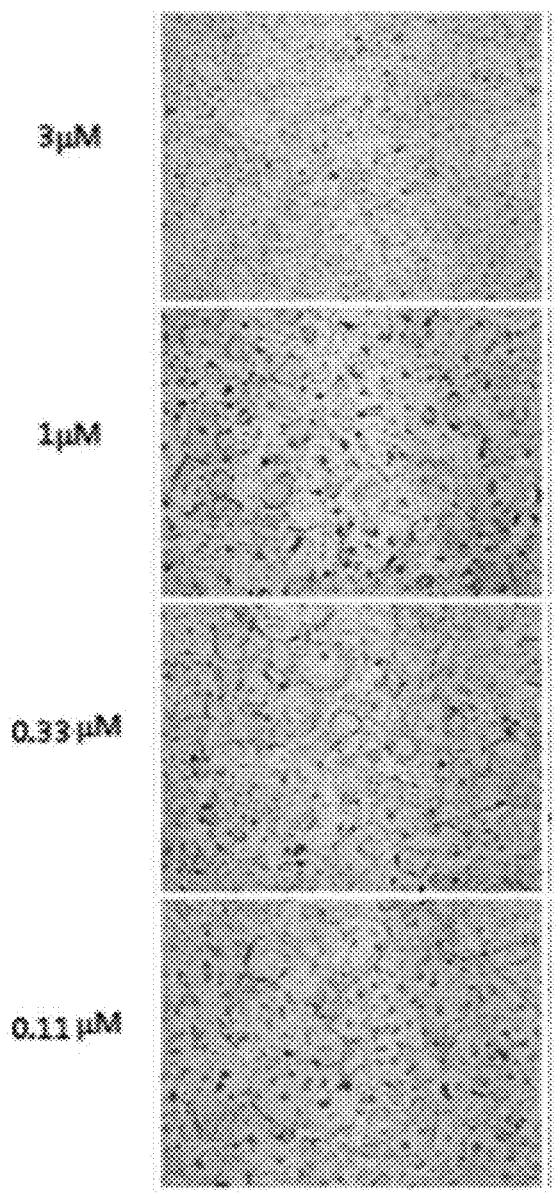
Figure 3:
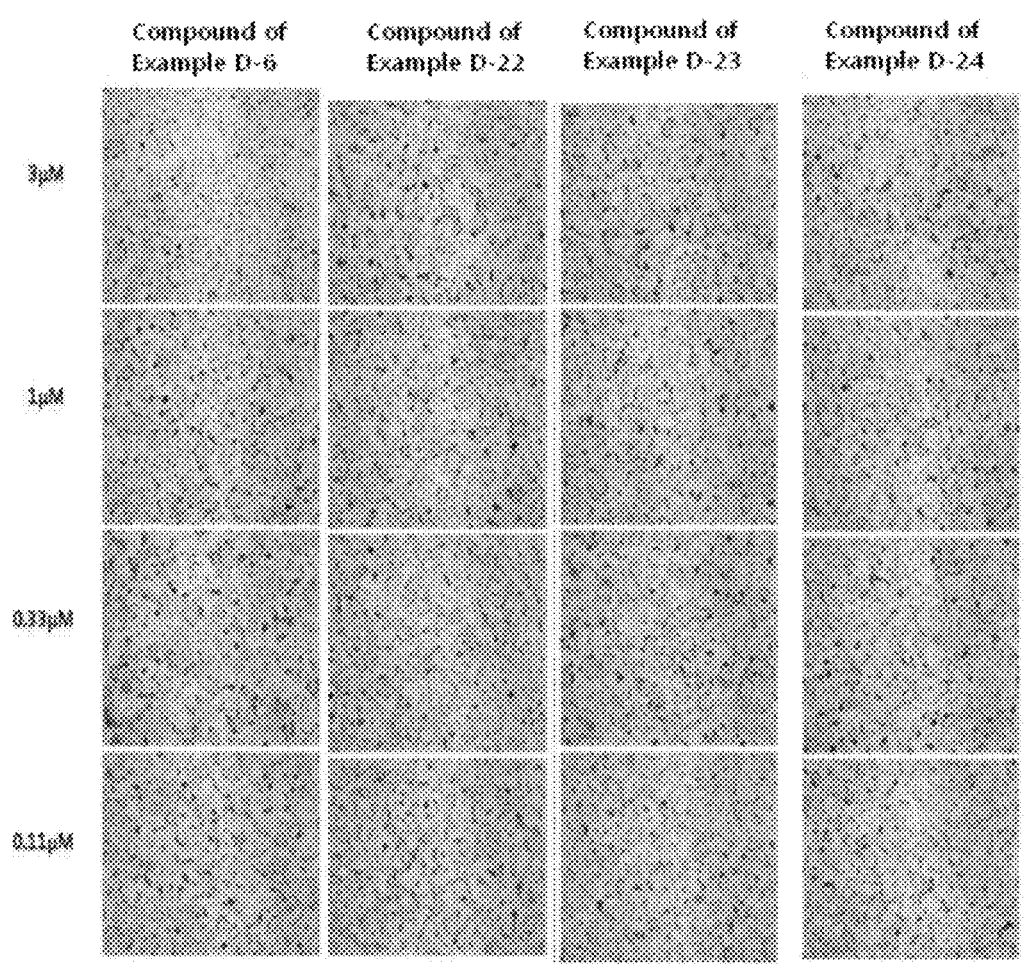
Figure 4:
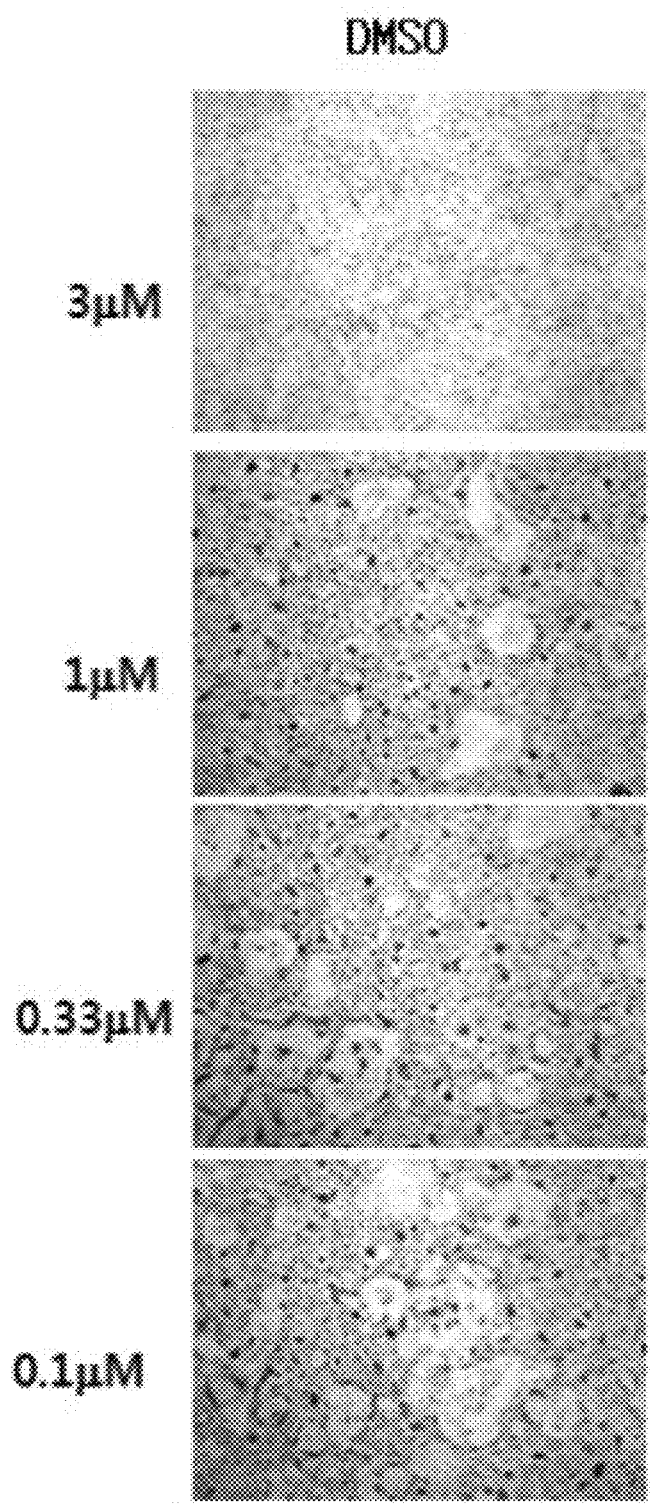

The results observed for macrophages cultured in the medium to which each of the compounds synthesized in Examples of the present invention was added are shown in FIGS. 1 to 3. The results observed for macrophages cultured in the medium to which DMSO was added are shown in FIG. 4.

As shown in FIGS. 1 to 4, the control group with the addition of DMSO exhibited differentiation of macrophages into osteoclasts, whereas macrophages of the medium with the addition of compounds synthesized in Examples of the present invention did not exhibit normal differentiation thereof into osteoclasts.

Further, as the concentration of the compounds synthesized in Examples of the present invention became higher such as 0.1 µM, 0.33 µM, 1 µM and 3 µM, cellular differentiation into osteoclasts was further suppressed. Accordingly, it can be seen that the compounds of the present invention inhibit differentiation of macrophages into osteoclasts in a dose-dependent fashion.

What is claimed is:

1. A compound or a pharmaceutically acceptable salt thereof selected from:
- 1-(pyridin-2-yl)-3-(3-(trifluoromethyl)phenyl)-1H-pyrazol-5-ol,
- 1-(pyridin-2-yl)-3-(4-(trifluoromethyl)phenyl)-1H-pyrazol-5-ol,
- 3-(3-nitrophenyl)-1-(pyridin-2-yl)-1H-pyrazol-5-ol,
- 1-(pyridin-2-yl)-3-(3,4,5-trimethoxyphenyl)-1H-pyrazol-5-ol,
- 3-(2-fluorophenyl)-1-(pyridin-2-yl)-1H-pyrazol-5-ol,
- 3-(3-fluorophenyl)-1-(pyridin-2-yl)-1H-pyrazol-5-ol,
- 3-(4-fluorophenyl)-1-(pyridin-2-yl)-1H-pyrazol-5-ol,
- 3-(2-chlorophenyl)-1-(pyridin-2-yl)-1H-pyrazol-5-ol,
- 3-(3-chlorophenyl)-1-(pyridin-2-yl)-1H-pyrazol-5-ol,
- 3-(4-chlorophenyl)-1-(pyridin-2-yl)-1H-pyrazol-5-ol,
- 3-(3-bromophenyl)-1-(pyridin-2-yl)-1H-pyrazol-5-ol,
- 3-(4-bromophenyl)-1-(pyridin-2-yl)-1H-pyrazol-5-ol,
- 3-(2-iodophenyl)-1-(pyridin-2-yl)-1H-pyrazol-5-ol,
- 3-(3-iodophenyl)-1-(pyridin-2-yl)-1H-pyrazol-5-ol,
- 3-(4-iodophenyl)-1-(pyridin-2-yl)-1H-pyrazol-5-ol,
- 3-(4-iodophenyl)-1-(pyrimidin-2-yl)-1H-pyrazol-5-ol,
- 2-(3-(4-iodophenyl)-5-(triisopropylsilyloxy)-1H-pyrazol-1-yl)pyridine,
- 3-(4-bromophenyl)-1-(pyridin-2-yl)-1H-pyrazol-5-yl tert-butyl carbonate,
- tert-butyl 3-(2-iodophenyl)-1-(pyridin-2-yl)-1H-pyrazol-5-yl carbonate,
- tert-butyl 3-(3-iodophenyl)-1-(pyridin-2-yl)-1H-pyrazol-5-yl carbonate,
- tert-butyl 3-(4-iodophenyl)-1-(pyridin-2-yl)-1H-pyrazol-5-yl carbonate,
- tert-butyl 3-(4-iodophenyl)-1-(pyrimidin-2-yl)-1H-pyrazol-5-yl carbonate,
- 3-(4-bromophenyl)-1-(pyridin-2-yl)-1H-pyrazol-5-yl acetate,
- 3-(biphenyl-4-yl)-1-(pyridin-2-yl)-1H-pyrazol-5-yl tert-butyl carbonate,
- 3-(4-(benzo[d][1,3]dioxol-5-yl)phenyl)-1-(pyridin-2-yl)-1H-pyrazol-5-yl tert-butyl carbonate,
- 3-(3'-phenylbiphenyl-4-yl)-1-(pyridin-2-yl)-1H-pyrazol-5-yl tert-butyl carbonate,
- tert-butyl 3-(4-(naphthalene)phenyl)-1-(pyridin-2-yl)-1H-pyrazol-5-yl carbonate,
- tert-butyl 3-(3'-(dimethylamino)biphenyl)-1-(pyridin-2-yl)-1H-pyrazol-5-yl carbonate,
- 3-(2-(benzo[d][1,3]dioxol-5-yl)phenyl)-1-(pyridin-2-yl)-1H-pyrazol-5-yl tert-butyl carbonate,
- 3-(3'-phenylbiphenyl-2-yl)-1-(pyridin-2-yl)-1H-pyrazol-5-yl tert-butyl carbonate,
- 3-(biphenyl-3-yl)-1-(pyridin-2-yl)-1H-pyrazol-5-yl tert-butyl carbonate,
- 3-(4'-(benzyloxy)biphenyl-3-yl)-1-(pyridin-2-yl)-1H-pyrazol-5-yl tert-butyl carbonate,
- 3-(4'-bromobiphenyl-3-yl)-1-(pyridin-2-yl)-1H-pyrazol-5-yl tert-butyl carbonate,
- tert-butyl 3-(3'-formylbiphenyl-3-yl)-1-(pyridin-2-yl)-1H-pyrazol-5-yl carbonate,
- tert-butyl 3-(2'-phenoxybiphenyl-3-yl)-1-(pyridin-2-yl)-1H-pyrazol-5-yl carbonate,
- 3-(3-(benzo[d][1,3]dioxol-5-yl)phenyl)-1-(pyridin-2-yl)-1H-pyrazol-5-yl tert-butyl carbonate,
- 3-(3'-phenylbiphenyl-3-yl)-1-(pyridin-2-yl)-1H-pyrazol-5-yl tert-butyl carbonate,
- tert-butyl 3-(3-(naphthalen-1-yl)phenyl)-1-(pyridin-2-yl)-1H-pyrazol-5-yl carbonate,
- tert-butyl 3-(3'-(dimethylamino)biphenyl-3-yl)-1-(pyridin-2-yl)-1H-pyrazol-5-yl carbonate,
- tert-butyl 3-(4'-methoxybiphenyl-4-yl)-1-(pyridin-2-yl)-1H-pyrazol-5-yl carbonate,
- 3-(4'-(benzyloxy)biphenyl-4-yl)-1-(pyridin-2-yl)-1H-pyrazol-5-yl tert-butyl carbonate,
- 3-(4'-bromobiphenyl-4-yl)-1-(pyridin-2-yl)-1H-pyrazol-5-yl tert-butyl carbonate,
- 3-(3'-formylbiphenyl-4-yl)-1-(pyridin-2-yl)-1H-pyrazol-5-yl tert-butyl carbonate,
- tert-butyl 3-(2'-phenoxybiphenyl-4-yl)-1-(pyridin-2-yl)-1H-pyrazol-5-yl carbonate,
- 3-(biphenyl-4-yl)-1-(pyrimidin-2-yl)-1H-pyrazol-5-yl tert-butyl carbonate,
- 3-(4-(benzo[d][1,3]dioxol-5-yl)phenyl)-1-(pyrimidin-2-yl)-1H-pyrazol-5-yl tert-butyl carbonate,
- 3-(3'-phenylbiphenyl-4-yl)-1-(pyrimidin-2-yl)-1H-pyrazol-5-yl tert-butyl carbonate,
- 2-(3-(4'-bromobiphenyl-4-yl)-5-(triisopropylsilyloxy)-1H-pyrazol-1-yl)pyridine,
- 2-(3-(biphenyl-4-yl)-5-(diphenylboryloxy)-1H-pyrazol-1-yl)pyridine,
- 3-(biphenyl-4-yl)-1-(pyridin-2-yl)-1H-pyrazol-5-ol,
- 3-(4-(benzo[d][1,3]dioxol-5-yl)phenyl)-1-(pyridin-2-yl)-1H-pyrazol-5-ol,
- 3-(3'-phenylbiphenyl-4-yl)-1-(pyridin-2-yl)-1H-pyrazol-5-ol,
- 3-(4-(naphthalen-1-yl)phenyl)-1-(pyridin-2-yl)-1H-pyrazol-5-ol,
- 3-(3'-(dimethylamino)biphenyl-4-yl)-1-(pyridin-2-yl)-1H-pyrazol-5-ol,
- 3-(2-(benzo[d][1,3]dioxol-5-yl)phenyl)-1-(pyridin-2-yl)-1H-pyrazol-5-ol,
- 3-(3'-phenylbiphenyl-2-yl)-1-(pyridin-2-yl)-1H-pyrazol-5-ol,
- 3-(biphenyl-3-yl)-1-(pyridin-2-yl)-1H-pyrazol-5-ol,
- 3-(4'-(benzyloxy)biphenyl-3-yl)-1-(pyridin-2-yl)-1H-pyrazol-5-ol,
- 3-(4'-bromobiphenyl-3-yl)-1-(pyridin-2-yl)-1H-pyrazol-5-ol,
- 3-(3'-formylbiphenyl-3-yl)-1-(pyridin-2-yl)-1H-pyrazol-5-ol,
- 3-(2'-phenoxybiphenyl-3-yl)-1-(pyridin-2-yl)-1H-pyrazol-5-ol,
- 3-(3-(benzo[d][1,3]dioxol-5-yl)phenyl)-1-(pyridin-2-yl)-1H-pyrazol-5-ol,
- 3-(3'-phenylbiphenyl-3-yl)-1-(pyridin-2-yl)-1H-pyrazol-5-ol,
- 3-(3-(naphthalen-1-yl)phenyl)-1-(pyridin-2-yl)-1H-pyrazol-5-ol,
- 3-(3'-(dimethylamino)biphenyl-3-yl)-1-(pyridin-2-yl)-1H-pyrazol-5-ol,
- 3-(4'-methoxybiphenyl-4-yl)-1-(pyridin-2-yl)-1H-pyrazol-5-ol,
- 3-(4'-(benzyloxy)biphenyl-4-yl)-1-(pyridin-2-yl)-1H-pyrazol-5-ol,
- 3-(4'-bromobiphenyl-4-yl)-1-(pyridin-2-yl)-1H-pyrazol-5-ol,
- 3-(3'-formylbiphenyl-4-yl)-1-(pyridin-2-yl)-1H-pyrazol-5-ol,
- 3-(2'-phenoxybiphenyl-4-yl)-1-(pyridin-2-yl)-1H-pyrazol-5-ol,
- 3-(biphenyl-4-yl)-1-(pyrimidin-2-yl)-1H-pyrazol-5-ol,
- 3-(4-(benzo[d][1,3]dioxol-5-yl)phenyl)-1-(pyrimidin-2-yl)-1H-pyrazol-5-ol,
- 3-(3'-phenylbiphenyl-4-yl)-1-(pyrimidin-2-yl)-1H-pyrazol-5-ol, and 4-benzyl-3-phenyl-1-(pyridin-2-yl)-1H-pyrazol-5-ol.

2. The compound according to claim 1, wherein the compound is a compound or a pharmaceutically acceptable salt thereof selected from:

3-(4-bromophenyl)-1-(pyridin-2-yl)-1H-pyrazol-5-ol, 3-(2-iodophenyl)-1-(pyridin-2-yl)-1H-pyrazol-5-ol, 3-(3-iodophenyl)-1-(pyridin-2-yl)-1H-pyrazol-5-ol, 3-(4-iodophenyl)-1-(pyridin-2-yl)-1H-pyrazol-5-ol, 3-(4-iodophenyl)-1-(pyrimidin-2-yl)-1H-pyrazol-5-ol, 2-(3-(4-iodophenyl)-5-(triisopropylsilyloxy)-1H-pyrazol-1-yl)pyridine, 3-(4-bromophenyl)-1-(pyridin-2-yl)-1H-pyrazol-5-yl acetate, 3-(biphenyl-4-yl)-1-(pyrimidin-2-yl)-1H-pyrazol-5-yl tert-butyl carbonate, 2-(3-(4'-bromobiphenyl-4-yl)-5-(triisopropylsilyloxy)-1H-pyrazol-1-yl)pyridine, 2-(3-(biphenyl-4-yl)-5-(diphenylboryloxy)-1H-pyrazol-1-yl)pyridine, 3-(biphenyl-4-yl)-1-(pyridin-2-yl)-1H-pyrazol-5-ol, 3-(4-(benzo[d][1,3]dioxol-5-yl)phenyl)-1-(pyridin-2-yl)-1H-pyrazol-5-ol, 3-(2-(benzo[d][1,3]dioxol-5-yl)phenyl)-1-(pyridin-2-yl)-1H-pyrazol-5-ol, 3-(biphenyl-3-yl)-1-(pyridin-2-yl)-1H-pyrazol-5-ol, 3-(2'-phenoxybiphenyl-3-yl)-1-(pyridin-2-yl)-1H-pyrazol-5-ol, 3-(3'-phenylbiphenyl-3-yl)-1-(pyridin-2-yl)-1H-pyrazol-5-ol, 3-(4'-bromobiphenyl-4-yl)-1-(pyridin-2-yl)-1H-pyrazol-5-ol, 3-(2'-phenoxybiphenyl-4-yl)-1-(pyridin-2-yl)-1H-pyrazol-5-ol, 3-(biphenyl-4-yl)-1-(pyrimidin-2-yl)-1H-pyrazol-5-ol, and 4-benzyl-3-phenyl-1-(pyridin-2-yl)-1H-pyrazol-5-ol.

3. A method for preparing a compound of formula I-2, comprising reacting a compound of formula I-1 with one compound selected from acetyl chloride, tris($C_1$-$C_4$) alkylsilyl chloride and di-tert-butyl dicarbonate (BOC$_2$O), in the presence of a base:

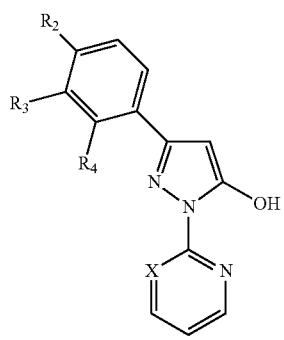

[Formula I-1]

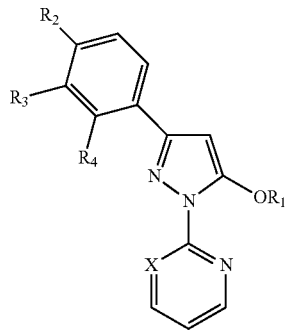

[Formula I-2]

wherein X represents —CH— or nitrogen;
$R_1$ represents an acetyl group, a tri($C_1$-$C_4$) alkylsilanyl group or a (t-butoxy)carbonyl group; and
$R_2$, $R_3$ and $R_4$ each independently represent a hydrogen atom, a halogen atom, a halo($C_1$-$C_3$) alkyl group or a ($C_2$-$C_6$) alkoxy group, provided that all of $R_2$, $R_3$ and $R_4$ are not a hydrogen atom at the same time.

4. The method according to claim 3, wherein the base is selected from 4-dimethylaminopyridine (DMAP), pyridine, triethylamine and imidazole.

5. A method for preparing a compound of formula I-3, comprising reacting a compound of formula I-2 with a compound of formula IV in the presence of a palladium metal catalyst and a base:

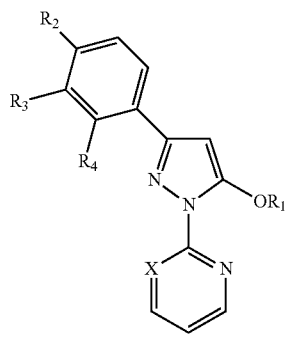

[Formula I-2]

wherein X represents —CH— or nitrogen;
$R_1$ represents hydrogen, an acetyl group, a tri($C_1$-$C_4$) alkylsilanyl group or a (t-butoxy)carbonyl group; and
$R_2$, $R_3$ and $R_4$ each independently represent a hydrogen atom or a halogen atom, provided that all of $R_2$, $R_3$ and $R_4$ are not a hydrogen atom at the same time;

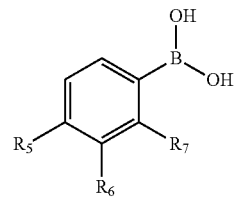

[Formula IV]

wherein $R_5$, $R_6$ and $R_7$ each independently represent a hydrogen atom, a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group, a phenyl group or a halogen-substituted phenyl group, or alternatively $R_5$ and $R_6$ or $R_6$ and $R_7$ represent —OCH$_2$O— or —CH=CH—CH=CH—, provided that all of $R_5$, $R_6$ and $R_7$ are not a hydrogen atom at the same time;

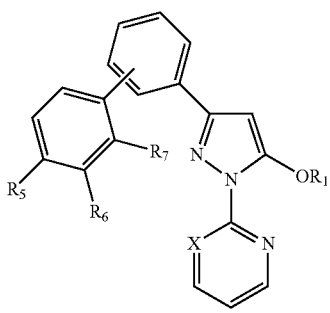

[Formula I-3]

wherein X represents —CH— or nitrogen;

$R_1$ represents hydrogen, an acetyl group, a tri($C_1$-$C_4$) alkylsilanyl group, a diphenylboranyl group or a (t-butoxy)carbonyl group; and $R_5$, $R_6$ and $R_7$ each independently represent a hydrogen atom, a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group, a phenyl group or a halogen-substituted phenyl group, or alternatively $R_5$ and $R_6$ or $R_6$ and $R_7$ represent —OCH$_2$O— or —CH=CH—CH=CH—, provided that all of $R_5$, $R_6$ and $R_7$ are not a hydrogen atom at the same time.

6. The method according to claim 5, wherein the palladium metal catalyst is 1,1'-bis(diphenylphosphino)ferrocene (dppf) and PdCl$_2$(dppf), and the base is selected from $K_3PO_4$, $K_2CO_3$, Ba(OH)$_2$ and $Cs_2CO_3$.

7. The method according to claim 5, wherein the reaction temperature is in the range of 90 to 110° C.

8. A method for preparing a compound of formula I-4, comprising converting a compound of formula I-3 into the compound of formula I-4 in the presence of an organic acid:

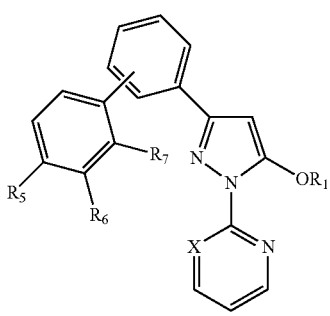

[Formula I-3]

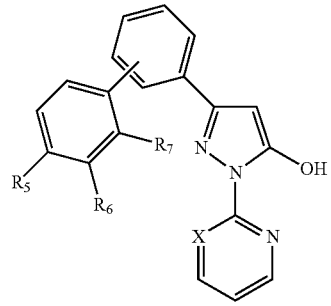

[Formula I-4]

wherein X represents —CH— or nitrogen;

$R_1$ represents an acetyl group, a tri($C_1$-$C_4$) alkylsilanyl group, a diphenylboranyl group or a (t-butoxy)carbonyl group;

$R_5$, $R_6$ and $R_7$ each independently represent a hydrogen atom, a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group, a phenyl group or a halogen-substituted phenyl group, or alternatively $R_5$ and $R_6$ or $R_6$ and $R_7$ represent —OCH$_2$O— or —CH=CH—CH=CH—, provided that all of $R_5$, $R_6$ and $R_7$ are not a hydrogen atom at the same time.

9. The method according to claim 8, wherein the organic acid is selected from trifluoroacetic acid, trichloroacetic acid, HF and HCl.

10. A pharmaceutical composition for the treatment of osteoporosis, comprising a compound of formula I:

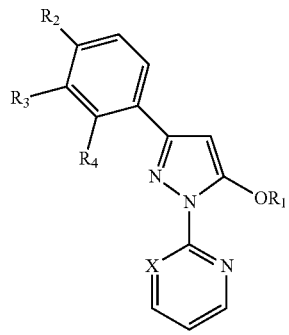

[Formula I]

wherein X represents —CH— or nitrogen;

$R_1$ represents a hydrogen atom, an acetyl group, a tri($C_1$-$C_4$) alkylsilanyl group, a diphenylboranyl group or a (t-butoxy)carbonyl group; and $R_2$, $R_3$ and $R_4$ each independently represent a hydrogen atom, a halogen atom, a halo($C_1$-$C_3$) alkyl group, a ($C_1$-$C_6$) alkoxy group, a benzo[d][1,3]dioxole group, an unsubstituted or substituted biphenyl group or an unsubstituted or substituted ($C_6$-$C_{10}$) aryl group, wherein the substituent is a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group or a halogen-substituted phenyl group, provided that all of $R_2$, $R_3$ and $R_4$ are not a hydrogen atom at the same time; or a pharmaceutically acceptable salt thereof.

11. A composition for the treatment of osteoporosis, comprising a compound or a pharmaceutically acceptable salt thereof selected from:

1-(pyridin-2-yl)-3-(3-(trifluoromethyl)phenyl)-1H-pyrazol-5-ol,
1-(pyridin-2-yl)-3-(4-(trifluoromethyl)phenyl)-1H-pyrazol-5-ol,
3-(3-nitrophenyl)-1-(pyridin-2-yl)-1H-pyrazol-5-ol,
3-(4-nitrophenyl)-1-(pyridin-2-yl)-1H-pyrazol-5-ol,
3-(4-methoxyphenyl)-1-(pyridin-2-yl)-1H-pyrazol-5-ol,
3-(3,4-dimethoxyphenyl)-1-(pyridin-2-yl)-1H-pyrazol-5-ol,
1-(pyridin-2-yl)-3-(3,4,5-trimethoxyphenyl)-1H-pyrazol-5-ol,
3-(2-fluorophenyl)-1-(pyridin-2-yl)-1H-pyrazol-5-ol,
3-(3-fluorophenyl)-1-(pyridin-2-yl)-1H-pyrazol-5-ol,
3-(4-fluorophenyl)-1-(pyridin-2-yl)-1H-pyrazol-5-ol,
3-(2-chlorophenyl)-1-(pyridin-2-yl)-1H-pyrazol-5-ol,
3-(3-chlorophenyl)-1-(pyridin-2-yl)-1H-pyrazol-5-ol,
3-(4-chlorophenyl)-1-(pyridin-2-yl)-1H-pyrazol-5-ol,
3-(3-bromophenyl)-1-(pyridin-2-yl)-1H-pyrazol-5-ol,
3-(4-bromophenyl)-1-(pyridin-2-yl)-1H-pyrazol-5-ol,
3-(2-iodophenyl)-1-(pyridin-2-yl)-1H-pyrazol-5-ol,
3-(3-iodophenyl)-1-(pyridin-2-yl)-1H-pyrazol-5-ol,
3-(4-iodophenyl)-1-(pyridin-2-yl)-1H-pyrazol-5-ol,
3-(4-iodophenyl)-1-(pyrimidin-2-yl)-1H-pyrazol-5-ol,
2-(3-(4-iodophenyl)-5-(triisopropylsilyloxy)-1H-pyrazol-1-yl)pyridine,
3-(4-bromophenyl)-1-(pyridin-2-yl)-1H-pyrazol-5-yl tert-butyl carbonate,
tert-butyl 3-(2-iodophenyl)-1-(pyridin-2-yl)-1H-pyrazol-5-yl carbonate,
tert-butyl 3-(3-iodophenyl)-1-(pyridin-2-yl)-1H-pyrazol-5-yl carbonate,
tert-butyl 3-(4-iodophenyl)-1-(pyridin-2-yl)-1H-pyrazol-5-yl carbonate,
tert-butyl 3-(4-iodophenyl)-1-(pyrimidin-2-yl)-1H-pyrazol-5-yl carbonate,
3-(4-bromophenyl)-1-(pyridin-2-yl)-1H-pyrazol-5-yl acetate,
3-(biphenyl-4-yl)-1-(pyridin-2-yl)-1H-pyrazol-5-yl tert-butyl carbonate,
3-(4-(benzo[d][1,3]dioxol-5-yl)phenyl)-1-(pyridin-2-yl)-1H-pyrazol-5-yl tert-butyl carbonate,
3-(3'-phenylbiphenyl-4-yl)-1-(pyridin-2-yl)-1H-pyrazol-5-yl tert-butyl carbonate,
tert-butyl 3-(4-(naphthalene)phenyl)-1-(pyridin-2-yl)-1H-pyrazol-5-yl carbonate,
tert-butyl 3-(3'-(dimethylamino)biphenyl)-1-(pyridin-2-yl)-1H-pyrazol-5-yl carbonate,
3-(2-(benzo[d][1,3]dioxol-5-yl)phenyl)-1-(pyridin-2-yl)-1H-pyrazol-5-yl tert-butyl carbonate,
3-(3'-phenylbiphenyl-2-yl)-1-(pyridin-2-yl)-1H-pyrazol-5-yl tert-butyl carbonate,
3-(biphenyl-3-yl)-1-(pyridin-2-yl)-1H-pyrazol-5-yl tert-butyl carbonate,
3-(4'-(benzyloxy)biphenyl-3-yl)-1-(pyridin-2-yl)-1H-pyrazol-5-yl tert-butyl carbonate,
3-(4'-bromobiphenyl-3-yl)-1-(pyridin-2-yl)-1H-pyrazol-5-yl tert-butyl carbonate,
tert-butyl 3-(3'-formylbiphenyl-3-yl)-1-(pyridin-2-yl)-1H-pyrazol-5-yl carbonate,
tert-butyl 3-(2'-phenoxybiphenyl-3-yl)-1-(pyridin-2-yl)-1H-pyrazol-5-yl carbonate,
3-(3-(benzo[d][1,3]dioxol-5-yl)phenyl)-1-(pyridin-2-yl)-1H-pyrazol-5-yl tert-butyl carbonate,
3-(3'-phenylbiphenyl-3-yl)-1-(pyridin-2-yl)-1H-pyrazol-5-yl tert-butyl carbonate,
tert-butyl 3-(3-(naphthalen-1-yl)phenyl)-1-(pyridin-2-yl)-1H-pyrazol-5-yl carbonate,
tert-butyl 3-(3'-(dimethylamino)biphenyl-3-yl)-1-(pyridin-2-yl)-1H-pyrazol-5-yl carbonate,
tert-butyl 3-(4'-methoxybiphenyl-4-yl)-1-(pyridin-2-yl)-1H-pyrazol-5-yl carbonate,
3-(4'-(benzyloxy)biphenyl-4-yl)-1-(pyridin-2-yl)-1H-pyrazol-5-yl tert-butyl carbonate,
3-(4'-bromobiphenyl-4-yl)-1-(pyridin-2-yl)-1H-pyrazol-5-yl tert-butyl carbonate,
3-(3'-formylbiphenyl-4-yl)-1-(pyridin-2-yl)-1H-pyrazol-5-yl tert-butyl carbonate,
tert-butyl 3-(2'-phenoxybiphenyl-4-yl)-1-(pyridin-2-yl)-1H-pyrazol-5-yl carbonate,
3-(biphenyl-4-yl)-1-(pyrimidin-2-yl)-1H-pyrazol-5-yl tert-butyl carbonate,
3-(4-(benzo[d][1,3]dioxol-5-yl)phenyl)-1-(pyrimidin-2-yl)-1H-pyrazol-5-yl tert-butyl carbonate,
3-(3'-phenylbiphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(3'-phenylbiphenyl-4-yl)-1-(pyridin-2-yl)-1H-pyrazol-5-ol,
3-(4-(naphthalen-1-yl)phenyl)-1-(pyridin-2-yl)-1H-pyrazol-5-ol,
3-(3'-(dimethylamino)biphenyl-4-yl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(3'-phenylbiphenyl-2-yl)-1-(pyridin-2-yl)-1H-pyrazol-5-ol,
3-(biphenyl-3-yl)-1-(pyridin-2-yl)-1H-pyrazol-5-ol,
3-(4'-(benzyloxy)biphenyl-3-yl)-1-(pyridin-2-yl)-1H-pyrazol-5-ol,
3-(4'-bromobiphenyl-3-yl)-1-(pyridin-2-yl)-1H-pyrazol-5-ol,
3-(3'-formylbiphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3-(benzo[d][1,3]dioxol-5-yl)phenyl)-1-(pyridin-2-yl)-1H-pyrazol-5-ol,
3-(3'-phenylbiphenyl-3-yl)-1-(pyridin-2-yl)-1H-pyrazol-5-ol,
3-(3-(naphthalen-1-yl)phenyl)-1-(pyridin-2-yl)-1H-pyrazol-5-ol,
3-(3'-(dimethylamino)biphenyl-3-yl)-1-(pyridin-2-yl)-1H-pyrazol-5-ol,
3-(4'-methoxybiphenyl-4-yl)-1-(pyridin-2-yl)-1H-pyrazol-5-ol,
3-(4'-(benzyloxy)biphenyl-4-yl)-1-(pyridin-2-yl)-1H-pyrazol-5-ol,
3-(4'-bromobiphenyl-4-yl)-1-(pyridin-2-yl)-1H-pyrazol-5-ol,
3-(3'-formylbiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol,
3-(biphenyl-4-yl)-1-(pyrimidin-2-yl)-1H-pyrazol-5-ol,
3-(4-(benzo[d][1,3]dioxol-5-yl)phenyl)-1-(pyrimidin-2-yl)-1H-pyrazol-5-ol, 3-(3'-phenylbiphenyl-4-yl)-1-(pyrimidin-2-yl)-1H-pyrazol-5-ol, and 4-benzyl-3-phenyl-1-(pyridin-2-yl)-1H-pyrazol-5-ol.

12. The composition according to claim 11, comprising a compound or a pharmaceutically acceptable salt thereof selected from:

3-(4-bromophenyl)-1-(pyridin-2-yl)-1H-pyrazol-5-ol, 3-(2-iodophenyl)-1-(pyridin-2-yl)-1H-pyrazol-5-ol, 3-(3-iodophenyl)-1-(pyridin-2-yl)-1H-pyrazol-5-ol, 3-(4-iodophenyl)-1-(pyridin-2-yl)-1H-pyrazol-5-ol, 3-(4-iodophenyl)-1-(pyrimidin-2-yl)-1H-pyrazol-5-ol, 2-(3-(4-iodophenyl)-5-(triisopropylsilyloxy)-1H-pyrazol-1-yl)pyridine, 3-(4-bromophenyl)-1-(pyridin-2-yl)-1H-pyrazol-5-yl acetate, 3-(biphenyl-4-yl)-1-(pyrimidin-2-yl)-1H-pyrazol-5-yl-tert-butyl carbonate, 2-(3-(4'-bromobiphenyl-4-yl)-5-(triisopropylsilyloxy)-1H-pyrazol-1-yl)pyridine, 2-(3-(biphenyl-4-yl)-5-(diphenylboryloxy)-1H-pyrazol-1-yl)pyridine, 3-(biphenyl-4-yl)-1-(pyridin-2-yl)-1H-pyrazol-5-ol, 3-(4-(benzo[d][1,3]dioxol-5-yl)phenyl)-1-(pyridin-2-yl)-1H-pyrazol-5-ol, 3-(2-(benzo[d][1,3]dioxol-5-yl)phenyl)-1-(pyridin-2-yl)-1H-pyrazol-5-ol, 3-(biphenyl-3-yl)-1-(pyridin-2-yl)-1H-pyrazol-5-ol, 3-(2'-phenoxybiphenyl-3-yl)-1-(pyridin-2-yl)-1H-pyrazol-5-ol, 3-(3'-phenylbiphenyl-3-yl)-1-(pyridin-2-yl)-1H-pyrazol-5-ol, 3-(4'-bromobiphenyl-4-yl)-1-(pyridin-2-yl)-1H-pyrazol-5-ol, 3-(2'-phenoxybiphenyl-4-yl)-1-(pyridin-2-yl)-1H-pyrazol-5-ol, 3-(biphenyl-4-yl)-1-(pyrimidin-2-yl)-1H-pyrazol-5-ol, and 4-benzyl-3-phenyl-1-(pyridin-2-yl)-1H-pyrazol-5-ol.

13. The composition according to claim 10, wherein the osteoporosis is post-menopausal osteoporosis.

14. A health food comprising the compound of claim 1 or a pharmaceutically acceptable salt thereof.

15. The composition according to claim 10, wherein the compound represented by formula I or a pharmaceutically acceptable salt thereof inhibits the generation of reactive oxygen species.

16. The composition according to claim 10, wherein the compound represented by formula I or a pharmaceutically acceptable salt thereof inhibits the production of osteoclasts.

17. A method for treating osteoporosis, comprising administering a composition containing a compound represented by formula I or a pharmaceutically acceptable salt thereof to a subject.

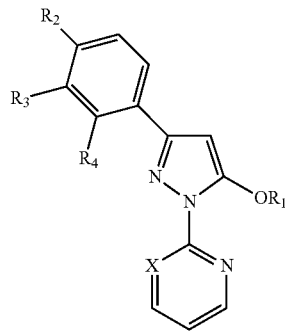

[Formula I]

wherein X represents —CH— or nitrogen;

$R_1$ represents a hydrogen atom, an acetyl group, a tri($C_1$-$C_4$) alkylsilanyl group, a diphenylboranyl group or a (t-butoxy)carbonyl group; and $R_2$, $R_3$ and $R_4$ each independently represent a hydrogen atom, a halogen atom, a halo($C_1$-$C_3$) alkyl group, a ($C_1$-$C_6$) alkoxy group, a benzo[d][1,3]dioxole group, an unsubstituted or substituted biphenyl group or an unsubstituted or substituted ($C_6$-$C_{10}$) aryl group, wherein the substituent is a halogen atom, a ($C_1$-$C_4$) alkylamine group, a halo($C_1$-$C_3$) alkyl group, a ($C_1$-$C_6$) alkoxy group, a phenoxy group, a benzyloxy group, a formyl group or a halogen-substituted phenyl group, provided that all of $R_2$, $R_3$ and $R_4$ are not a hydrogen atom at the same time.

18. The method of claim 17 wherein the compound represented by formula I or a pharmaceutically acceptable salt thereof is selected from:

1-(pyridin-2-yl)-3-(3-(trifluoromethyl)phenyl)-1H-pyrazol-5-ol, 1-(pyridin-2-yl)-3-(4-(trifluoromethyl)phenyl)-1H-pyrazol-5-ol, 3-(3-nitrophenyl)-1-(pyridin-2-yl)-1H-pyrazol-5-ol, 3-(4-nitrophenyl)-1-(pyridin-2-yl)-1H-pyrazol-5-ol, 3-(4-methoxyphenyl)-1-(pyridin-2-yl)-1H-pyrazol-5-ol, 3-(3,4-dimethoxyphenyl)-1-(pyridin-2-yl)-1H-pyrazol-5-ol, 1-(pyridin-2-yl)-3-(3,4,5-trimethoxyphenyl)-1H-pyrazol-5-ol, 3-(2-fluorophenyl)-1-(pyridin-2-yl)-1H-pyrazol-5-ol, 3-(3-fluorophenyl)-1-(pyridin-2-yl)-1H-pyrazol-5-ol, 3-(4-fluorophenyl)-1-(pyridin-2-yl)-1H-pyrazol-5-ol, 3-(2-chlorophenyl)-1-(pyridin-2-yl)-1H-pyrazol-5-ol, 3-(3-chlorophenyl)-1-(pyridin-2-yl)-1H-pyrazol-5-ol, 3-(4-chlorophenyl)-1-(pyridin-2-yl)-1H-pyrazol-5-ol, 3-(3-bromophenyl)-1-(pyridin-2-yl)-1H-pyrazol-5-ol, 3-(4-bromophenyl)-1-(pyridin-2-yl)-1H-pyrazol-5-ol, 3-(2-iodophenyl)-1-(pyridin-2-yl)-1H-pyrazol-5-ol, 3-(3-iodophenyl)-1-(pyridin-2-yl)-1H-pyrazol-5-ol, 3-(4-iodophenyl)-1-(pyridin-2-yl)-1H-pyrazol-5-ol, 3-(4-iodophenyl)-1-(pyrimidin-2-yl)-1H-pyrazol-5-ol, 2-(3-(4-iodophenyl)-5-(triisopropylsilyloxy)-1H-pyrazol-1-yl)pyridine, 3-(4-bromophenyl)-1-(pyridin-2-yl)-1H-pyrazol-5-yl tert-butyl carbonate, tert-butyl 3-(2-iodophenyl)-1-(pyridin-2-yl)-1H-pyrazol-5-yl carbonate, tert-butyl 3-(3-iodophenyl)-1-(pyridin-2-yl)-1H-pyrazol-5-yl carbonate, tert-butyl 3-(4-iodophenyl)-1-(pyridin-2-yl)-1H-pyrazol-5-yl carbonate, tert-butyl 3-(4-iodophenyl)-1-(pyrimidin-2-yl)-1H-pyrazol-5-yl carbonate,
3-(4-bromophenyl)-1-(pyridin-2-yl)-1H-pyrazol-5-yl acetate,
3-(biphenyl-4-yl)-1-(pyridin-2-yl)-1H-pyrazol-5-yl tert-butyl carbonate,
3-(4-(benzo[d][1,3]dioxol-5-yl)phenyl)-1-(pyridin-2-yl)-1H-pyrazol-5-yl tert-butyl carbonate,
3-(3'-phenylbiphenyl-4-yl)-1-(pyridin-2-yl)-1H-pyrazol-5-yl tert-butyl carbonate,
tert-butyl 3-(4-(naphthalene)phenyl)-1-(pyridin-2-yl)-1H-pyrazol-5-yl carbonate,
tert-butyl 3-(3'-(dimethylamino)biphenyl)-1-(pyridin-2-yl)-1H-pyrazol-5-yl carbonate,
3-(2-(benzo[d][1,3]dioxol-5-yl)phenyl)-1-(pyridin-2-yl)-1H-pyrazol-5-yl tert-butyl carbonate,
3-(3'-phenylbiphenyl-2-yl)-1-(pyridin-2-yl)-1H-pyrazol-5-yl tert-butyl carbonate,
3-(biphenyl-3-yl)-1-(pyridin-2-yl)-1H-pyrazol-5-yl tert-butyl carbonate,
3-(4'-(benzyloxy)biphenyl-3-yl)-1-(pyridin-2-yl)-1H-pyrazol-5-yl tert-butyl carbonate,
3-(4'-bromobiphenyl-3-yl)-1-(pyridin-2-yl)-1H-pyrazol-5-yl tert-butyl carbonate,
tert-butyl 3-(3'-formylbiphenyl-3-yl)-1-(pyridin-2-yl)-1H-pyrazol-5-yl carbonate,
tert-butyl 3-(2'-phenoxybiphenyl-3-yl)-1-(pyridin-2-yl)-1H-pyrazol-5-yl carbonate,
3-(3-(benzo[d][1,3]dioxol-5-yl)phenyl)-1-(pyridin-2-yl)-1H-pyrazol-5-yl tert-butyl carbonate,
3-(3'-phenylbiphenyl-3-yl)-1-(pyridin-2-yl)-1H-pyrazol-5-yl tert-butyl carbonate,
tert-butyl 3-(3-(naphthalen-1-yl)phenyl)-1-(pyridin-2-yl)-1H-pyrazol-5-yl carbonate,
tert-butyl 3-(3'-(dimethylamino)biphenyl-3-yl)-1-(pyridin-2-yl)-1H-pyrazol-5-yl carbonate,
tert-butyl 3-(4'-methoxybiphenyl-4-yl)-1-(pyridin-2-yl)-1H-pyrazol-5-yl carbonate,
3-(4'-(benzyloxy)biphenyl-4-yl)-1-(pyridin-2-yl)-1H-pyrazol-5-yl tert-butyl carbonate,
3-(4'-bromobiphenyl-4-yl)-1-(pyridin-2-yl)-1H-pyrazol-5-yl tert-butyl carbonate,
3-(3'-formylbiphenyl-4-yl)-1-(pyridin-2-yl)-1H-pyrazol-5-yl tert-butyl carbonate,
tert-butyl 3-(2'-phenoxybiphenyl-4-yl)-1-(pyridin-2-yl)-1H-pyrazol-5-yl carbonate,
3-(biphenyl-4-yl)-1-(pyrimidin-2-yl)-1H-pyrazol-5-yl tert-butyl carbonate,
3-(4-(benzo[d][1,3]dioxol-5-yl)phenyl)-1-(pyrimidin-2-yl)-1H-pyrazol-5-yl tert-butyl carbonate,
3-(3'-phenylbiphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(3'-phenylbiphenyl-4-yl)-1-(pyridin-2-yl)-1H-pyrazol-5-ol,
3-(4-(naphthalen-1-yl)phenyl)-1-(pyridin-2-yl)-1H-pyrazol-5-ol,
3-(3'-(dimethylamino)biphenyl-4-yl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(3'-phenylbiphenyl-2-yl)-1-(pyridin-2-yl)-1H-pyrazol-5-ol,
3-(biphenyl-3-yl)-1-(pyridin-2-yl)-1H-pyrazol-5-ol,
3-(4'-(benzyloxy)biphenyl-3-yl)-1-(pyridin-2-yl)-1H-pyrazol-5-ol,
3-(4'-bromobiphenyl-3-yl)-1-(pyridin-2-yl)-1H-pyrazol-5-ol,
3-(3'-formylbiphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3-(benzo[d][1,3]dioxol-5-yl)phenyl)-1-(pyridin-2-yl)-1H-pyrazol-5-ol,
3-(3'-phenylbiphenyl-3-yl)-1-(pyridin-2-yl)-1H-pyrazol-5-ol,
3-(3-(naphthalen-1-yl)phenyl)-1-(pyridin-2-yl)-1H-pyrazol-5-ol,
3-(3'-(dimethylamino)biphenyl-3-yl)-1-(pyridin-2-yl)-1H-pyrazol-5-ol,
3-(4'-methoxybiphenyl-4-yl)-1-(pyridin-2-yl)-1H-pyrazol-5-ol,
3-(4'-(benzyloxy)biphenyl-4-yl)-1-(pyridin-2-yl)-1H-pyrazol-5-ol,
3-(4'-bromobiphenyl-4-yl)-1-(pyridin-2-yl)-1H-pyrazol-5-ol,
3-(3'-formylbiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol,
3-(biphenyl-4-yl)-1-(pyrimidin-2-yl)-1H-pyrazol-5-ol,
3-(4-(benzo[d][1,3]dioxol-5-yl)phenyl)-1-(pyrimidin-2-yl)-1H-pyrazol-5-ol,
3-(3'-phenylbiphenyl-4-yl)-1-(pyrimidin-2-yl)-1H-pyrazol-5-ol, and
4-benzyl-3-phenyl-1-(pyridin-2-yl)-1H-pyrazol-5-ol.

19. The method of claim 18 wherein the compound represented by formula I or a pharmaceutically acceptable salt thereof is selected from:
3-(4-bromophenyl)-1-(pyridin-2-yl)-1H-pyrazol-5-ol,
3-(2-iodophenyl)-1-(pyridin-2-yl)-1H-pyrazol-5-ol,
3-(3-iodophenyl)-1-(pyridin-2-yl)-1H-pyrazol-5-ol,
3-(4-iodophenyl)-1-(pyridin-2-yl)-1H-pyrazol-5-ol,
3-(4-iodophenyl)-1-(pyrimidin-2-yl)-1H-pyrazol-5-ol,
2-(3-(4-iodophenyl)-5-(triisopropylsilyloxy)-1H-pyrazol-1-yl)pyridine,
3-(4-bromophenyl)-1-(pyridin-2-yl)-1H-pyrazol-5-yl acetate,
3-(biphenyl-4-yl)-1-(pyrimidin-2-yl)-1H-pyrazol-5-yl tert-butyl carbonate,
2-(3-(4'-bromobiphenyl-4-yl)-5-(triisopropylsilyloxy)-1H-pyrazol-1-yl)pyridine,
2-(3-(biphenyl-4-yl)-5-(diphenylboryloxy)-1H-pyrazol-1-yl)pyridine,
3-(biphenyl-4-yl)-1-(pyridin-2-yl)-1H-pyrazol-5-ol,
3-(4-(benzo[d][1,3]dioxol-5-yl)phenyl)-1-(pyridin-2-yl)-1H-pyrazol-5-ol,
3-(2-(benzo[d][1,3]dioxol-5-yl)phenyl)-1-(pyridin-2-yl)-1H-pyrazol-5-ol,
3-(biphenyl-3-yl)-1-(pyridin-2-yl)-1H-pyrazol-5-ol,
3-(2'-phenoxybiphenyl-3-yl)-1-(pyridin-2-yl)-1H-pyrazol-5-ol,
3-(3'-phenylbiphenyl-3-yl)-1-(pyridin-2-yl)-1H-pyrazol-5-ol,
3-(4'-bromobiphenyl-4-yl)-1-(pyridin-2-yl)-1H-pyrazol-5-ol,
3-(2'-phenoxybiphenyl-4-yl)-1-(pyridin-2-yl)-1H-pyrazol-5-ol, 3-(biphenyl-4-yl)-1-(pyrimidin-2-yl)-1H-pyrazol-5-ol, and
4-benzyl-3-phenyl-1-(pyridin-2-yl)-1H-pyrazol-5-ol.

* * * * *